(12) United States Patent
Pampaloni et al.

(10) Patent No.: US 10,059,724 B2
(45) Date of Patent: Aug. 28, 2018

(54) PYRIDINE COMPLEX OF ZIRCONIUM, CATALYTIC SYSTEM COMPRISING SAID PYRIDINE COMPLEX OF ZIRCONIUM AND PROCESS OF (CO)POLYMERIZATION OF CONJUGATED DIENES

(71) Applicant: VERSALIS S.P.A., San Donato Milanese (MI) (IT)

(72) Inventors: Guido Pampaloni, Pontedera (IT); Giovanni Ricci, Parma (IT); Anna Sommazzi, Santa Margherita Ligure (IT); Francesco Masi, Sant'Angelo Lodigiano (IT); Giuseppe Leone, Milan (IT)

(73) Assignee: Versalis S.p.A., San Donato Milanese (IT)

( * ) Notice: Subject to any disclaimer, the term of this patent is extended or adjusted under 35 U.S.C. 154(b) by 0 days.

(21) Appl. No.: 15/512,332

(22) PCT Filed: Sep. 16, 2015

(86) PCT No.: PCT/EP2015/071189
§ 371 (c)(1),
(2) Date: Mar. 17, 2017

(87) PCT Pub. No.: WO2016/042014
PCT Pub. Date: Mar. 24, 2016

(65) Prior Publication Data
US 2017/0247397 A1 Aug. 31, 2017

(30) Foreign Application Priority Data
Sep. 17, 2014 (IT) .............................. MI2014A1596

(51) Int. Cl.
*C08F 4/64* (2006.01)
*C08F 4/76* (2006.01)
*C07F 7/00* (2006.01)
*C08F 136/06* (2006.01)
*C08F 4/60* (2006.01)

(52) U.S. Cl.
CPC ............ *C07F 7/006* (2013.01); *C08F 136/06* (2013.01); *C08F 4/60013* (2013.01); *C08F 4/64013* (2013.01)

(58) Field of Classification Search
CPC .............. C08F 4/60044; C08F 4/62044; C08F 4/64044
See application file for complete search history.

(56) References Cited

U.S. PATENT DOCUMENTS

| 5,128,295 | A | 7/1992 | Porri et al. |
| 5,258,475 | A | 11/1993 | Kissin et al. |
| 6,268,447 | B1 * | 7/2001 | Murray .................... C07F 7/00 502/155 |
| 6,927,263 | B2 * | 8/2005 | Peterson ................. C07F 7/006 526/132 |
| 7,122,689 | B2 * | 10/2006 | Boussie .................. C07F 7/006 556/51 |
| 7,199,255 | B2 * | 4/2007 | Murray .................... C07F 7/00 502/167 |
| 2002/0137845 | A1 * | 9/2002 | Boussie ............... C07D 213/38 525/170 |
| 2010/0022726 | A1 | 1/2010 | Hagadorn | |

FOREIGN PATENT DOCUMENTS

| DE | 2113527 | 10/1971 | |
| EP | 277033 | 8/1988 | |
| EP | 418044 | 3/1991 | |
| EP | 421659 | 4/1991 | |
| EP | 427697 | 5/1991 | |
| EP | 495375 | 7/1992 | |
| EP | 520732 | 12/1992 | |
| WO | 92/00333 | 1/1992 | |
| WO | 92/05208 | 4/1992 | |
| WO | WO 97/45434 A1 * | 12/1997 | ............... C09F 9/00 |
| WO | 2011061151 | 5/2011 | |

OTHER PUBLICATIONS

Annunziata, L.; Pappalardo, D.; Tedesco, C.; Pellacchia, C. Organometallics 2009, 28, 688-697.*
Annunziata, L.; Pragliola, S.; Pappalardo, D.; Tedesco, C.; Pellacchia, C. Macromolecules 2011, 44, 1934-1941.*
Nienkemper, K.; Kehr, G.; Kehr, S.; Frolich, R.; Erker, G. J. Organomet. Chem. 2008, 693,1572-1589.*
Annunziata, L.; Pappalardo, D.; Tedesco, C.; Pellechia, C. Organometallics 2009, 28, 688-697. (Year: 2009).*
Annunziata, L.; Prgliola, S.; Pappalardo, D.; Tedesco, C.; Pellechia, C. Macromolecules 2011, 44, 1934-1941. (Year: 2011).*
Nienkemper, K.; Kehr, G.; Kehr, S. Frolich, R.; Erker, G. J. Organomet. Chem. 2008, 693, 1572-1589. (Year: 2008).*
Annunziata L. et al., "Macromolecules" (2011), vol. 44, pp. 1934-1941.
Wu J. et al., "Journal of American Chemistry Society" (2009), vol. 131(36), pp. 12915-12917.
Laine V. T. et al., "European Journal of Inorganic Chemistry" (1999), vol. 6, pp. 959-964.

(Continued)

*Primary Examiner* — Rip A Lee
(74) *Attorney, Agent, or Firm* — Abel Law Group, LLP

(57) ABSTRACT

Pyridine complex of zirconium having general formula (I): Said pyridine complex of zirconium having general formula (I) may advantageously be used in a catalytic system for the (co)polymerization of conjugated dienes.

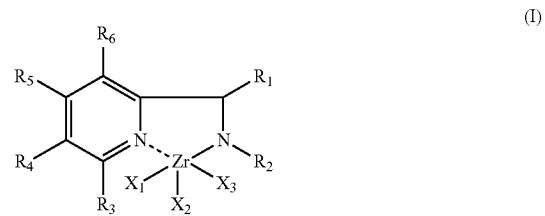

(I)

12 Claims, 18 Drawing Sheets

(56) References Cited

OTHER PUBLICATIONS

Bianchini C. et al., "New Journal of Chemistry" (2002), vol. 26(4), pp. 337-397.
Lai Yi-C. et al., "Tetrahedron" (2005), vol. 61(40), pp. 9434-9439.
Nienkemper K. et al., "Journal of Organometallic Chemistry" (2003), vol. 693(8-9), pp. 1572-1589.
Lin Y. et al., "Dalton Transactions" (2012), vol. 41(22), pp. 6661-6670.
K. Johnson et al., in "Journal of the American Chemical Society" (1995), vol. 117, pp. 6414-6415.
G. van Koteri et al., in "Advances in Organometallic Chemistry" (1982), vol. 21, pp. 151-239.
W. Beck et al., "Chemical Reviews" (1988), vol. 88, pp. 1405-1421.
S.H. Strauss, "Chemical Reviews" (1993), vol. 93, pp. 927-942.
Mochel, V.D., in "Journal of Polymer Science Part A-1: Polymer Chemistry" (1972), vol. 10, issue 4, pp. 1009-1018.
International Search Report dated Nov. 16, 2015 for PCT/EP2015/071189International Search Report dated Nov. 16, 2015 for PCT/EP2015/071189
"Periodic Table of the Elements" dated Jun. 22, 2007, available at the following Internet address: www.iupac.org/fileadmin/user_upload/news/IUPAC_Periodic_Table-1Jun12.pdf.
Annunziata L. et al, "Bis[(amidomethyl)pyridine] Zirconium(IV) Complexes: Synthesis, Characterization, and Activity as Olefin Polymerization Catalysts +", Organometallics, vol. 28, No. 3, Feb. 9, 2009 (Feb. 9, 2009), pp. 688-697.
Tshuva E. Y. et al, "Zirconium Complexes of Amine-Bis(Phenolate) Ligands As Catalysts for 1-Hexene Polymerization: Peripheral Structural Parameters Strongly Affect Reactivity" Organometallics, ACS, Washington DC, vol. 20, No. 14, Jul. 9, 2001, p. 3025.
Porri L. et al, "Comprehensive Polymer Science" (1989), Eastmond G.C. et al. Eds., Pergamon Press, Oxford, UK, vol. 4, Part II, pp. 53-108.
Thiele S. K. H. et al., "Journal of Macromolecular Science. Part C: Polymer Reviews" (2003), C43, pp. 581-628.
Osakada K. et al., "Advanced Polymer Science" (2004), vol. 171, pp. 137-194.
Ricci G. et al, "Advances in Organometallic Chemistry Research" (2007), Yamamoto K. Ed., Nova Science Publishers, Inc., USA, pp. 1-36.
Ricci G. et al., "Coordination Chemistry Reviews" (2010), vol. 254, pp. 661-676.
Friebe L. et al., "Advanced Polymer Science" (2006), vol. 204, pp. 1-154.
Home S. E. et al. in "Industrial & Engineering Chemistry" (1956), vol. 48(4), pp. 784-791.
Natta G. et al., "La Chimica a L'Industria" (1959), vol. 40, p. 362.
Natta G. et al., "La Chimica e L'Industria" (1959), vol. 41, p. 116.
Ricci G. et al., "Polymer Communication" (1991), vol. 32, pp. 514-517.
Ricci G. et al., "Journal of Polymer Science Part A: Polymer Chemistry" (2007), vol. 45, pp. 4635-4646.
Porri L. et al., "Die Makromolekulare Chemie" (1963), vol. 61(1), pp. 90-103.
Natta G. et al., "La Chimica e L'Industria" (1959), vol. 41, p. 526.
Porri L. et al., "Metalorganic Catalyst for Synthesis and Polymerization" (1999), Kaminsky W. Ed., Springer-Verlag Berlin Heidelberg, pp. 519-530.
Natta G. et al., "La Chimica e L'Industria" (1959), vol. 41, p. 1163.
Ricci G. et al., "Chromium: Environmental, Medical and Material Studies" (2011), Salden M. P. Ed. Nova Science Publishers Inc., USA, pp. 121-140.
Ricci G. et al., "Macromolecules" (2001), vol. 34, pp. 5766-5769.
Ricci G. et al., "Polymer Bullettin" (2002), vol. 48, pp. 25-31.
Ricci G. et al., "Organometallics" (2004), vol. 23(15), pp. 3727-3732.
Ricci G. et al., "Journal of Molecular Catalysis A: Chemical" (2007), vol. 267, pp. 102-107.
Ricci G. et al., "Macromolecular Symposia" (2004), vol. 260(1), pp. 172-178.
Bazzini C. et al., "Macromolecular Rapid Communications" (2002), vol. 23(15), pp. 922-927.
Ricci G. et al., "Journal of Molecular Catalysis A: Chemical" (2003), vol. 204-205, pp. 287-293.
Bazzini C. et al., "Polymer" (2004), vol. 45, pp. 2871-2875.
Ricci G. et al., "Ferrocenes: Compounds, Properties and Applications" (2011), Phillips E. S. Ed., Nova Science Publishers Inc., USA, pp. 273-314.
Ricci G. et al., "Cobalt: Characteristics, Compounds, and Applications" (2011), Lucas J. Vidmar Ed., Nova Science Publishers, Inc., USA, pp. 39-81.
Ricci G. et al., "Macromolecules" (2005), vol. 38, pp. 1064-1070.
Ricci G. et al., "Journal of Organometallic Chemistry" (2005), vol. 690, pp. 1845-1854.
Takeuchi M. et al., "Polymer International" (1992), vol. 29, pp. 209-212.
Takeuchi M. et al., "Polymer International" (1995), vol. 36, pp. 41-45.
Takeuchi M. et al., "Macromolecular Chemistry and Physics" (1996), vol. 197, pp. 729-743.
Longo P. et al., "Macromolecular Rapid Communications" (1998), vol. 19(1), pp. 31-34.
Throckmorton M. C. et al., "Rubber Chemistry and Technology" (1972), vol. 45, pp. 268-277.
Saltman W. et al., "Rubber Chemistry and Technology" (1973), vol. 46, pp. 1055-1067.
Wilson D. J. et al., "Polymer Bulletin" (1992), vol. 27, pp. 407-411.
Porri L. et al., "Macromolecular Symposia" (1998), vol. 128(1), pp. 53-61.

\* cited by examiner

FTIR-ATR spectrum of the ZrCl$_3$(L1) complex [sample BM2-199] (Example 8)

$^1$H-NMR spectrum of the ZrCl$_3$(L1) complex [sample BM2-199] (Example 8)

FTIR-ATR spectrum of the ZrCl$_3$(L2) complex [sample BM2-207] (Example 9)

$^1$H-NMR spectrum of the $ZrCl_3(L2)$ complex [sample BM2-207] (Example 9)

FTIR-ATR spectrum of the ZrCl$_3$(L5) complex [sample MT-4] (Example 11)

FT-IR spectra of the polybutadienes listed in Table 1: (a) GL957 (Example 16); (b) GL959 (Example 17); (c) MM20 (Example 18); (d) G1125 (Example 19); (e) MM21 (Example 21)

$^{13}$C-NMR spectrum of polybutadiene GL959 (Example 17)

¹H-NMR spectrum of polybutadiene MM20 (Example 18)

13C-NMR spectrum of polybutadiene MM20 (Example 18)

¹H-NMR spectrum of polybutadiene G1112 (Example 20)

$^{13}$C-NMR spectrum of polybutadiene G1112 (Example 20)

GPC diagram for polybutadiene GL959 (Example 17)

GPC diagram of polybutadiene MM20 (Example 18)

GPC diagram of polybutadiene MM21 (Example 21)

GPC diagram of polybutadiene G1120 (Example 22)

GPC diagram of polybutadiene G1121 (Example 23)

DSC diagram of polybutadiene G1121 (Example 23)

(Melting peak at 120.8°C and crystallization peak at 103.1°C; the peaks at 66.60°C and at 51.41°C relate to solid/solid phase transitions, typical of polybutadiene having 1,4-trans structure)

DSC diagram of polybutadiene MM20 (Example 18)

(Melting peak at 134.8°C and crystallization peak at 116.5°C; the peaks at 70.57°C and at 49.35°C relate to solid/solid phase transitions, typical of polybutadiene having 1,4-trans structure)

PYRIDINE COMPLEX OF ZIRCONIUM, CATALYTIC SYSTEM COMPRISING SAID PYRIDINE COMPLEX OF ZIRCONIUM AND PROCESS OF (CO)POLYMERIZATION OF CONJUGATED DIENES

The present invention relates to a pyridine complex of zirconium.

More particularly, the present invention relates to a pyridine complex of zirconium and to the use thereof in a catalytic system for the (co)polymerization of conjugated dienes.

The present invention further relates to a catalytic system for the (co)polymerization of conjugated dienes comprising said pyridine complex of zirconium.

Further, the present invention relates to a process of (co)polymerization of conjugated dienes, in particular a process of polymerization of 1,3-butadiene, characterized in that it uses said catalytic system.

It is known that stereospecific (co)polymerization of conjugated dienes is a very important process in the chemical industry for obtaining products which are among the most widely used rubbers.

Said stereospecific (co)polymerization may give polymers having a differing structure, namely 1,4-trans structure, 1,4-cis structure, 1,2 structure and, in the case of asymmetrical conjugated dienes (e.g., isoprene), 3,4 structure. The stereoregular polymers having 1,4-cis structure and 1,4-trans structure may further be isotactic or syndiotactic if there are asymmetric carbon atoms along the polymer chain, as for example in the case of the polymers derived from the polymerization of 1,3-pentadiene. Stereoregular polymers having 1,2 structure or 3,4 structure may also be isotactic or syndiotactic, and depending on the structure of the conjugated diene which is polymerized, the double bond in the polymer side chain may have 1,4-trans structure or 1,4-cis structure.

The aforementioned stereoregular polymers can only be obtained by stereospecific polymerization using catalytic systems of the Ziegler-Natta type, generally obtained by combining transition metal or lanthanide compounds such as, for example, halides, alcoholates, carboxylates, organometallic compounds having ligands of various types, with suitable alkylating agents, such as aluminium alkyls [e.g., $Al(R)_3$, in which R may be, for example, methyl, ethyl, n-propyl, iso-propyl, n-butyl, iso-butyl], or aluminoxanes [e.g., methylaluminoxane (MAO)]. This is because stereospecific polymerization, by contrast with other methods of polymerization (e.g., radical polymerization, anionic polymerization) is distinguished by: (i) high regioselectivity, namely it is able to provide polymers formed from a single type of structure (namely 1,4 structure, or 1,2 structure, or 3,4 structure); (ii) high stereoselectivity, namely it is able to provide polymers having a high configurational order if there are steric isomerism sites in the conjugated diene (e.g., an internal double bound, an asymmetric carbon atom). Further details regarding said stereospecific polymerization may be found, for example, in: Porri L. et al., "*Comprehensive Polymer Science*" (1989), Eastmond G. C. et al. Eds., Pergamon Press, Oxford, UK, Vol. 4, Part II, pp. 53-108; Thiele S. K. H. et al., "*Macromolecular Science. Part C: Polymer Reviews*" (2003), C43, pp. 581-628; Osakada K. et al., "*Advanced Polymer Science*" (2004), Vol. 171, pp. 137-194; Ricci G. et al., "*Advances in Organometallic Chemistry Research*" (2007), Yamamoto K. Ed., Nova Science Publishers, Inc., USA, pp. 1-36; Ricci G. et al., "*Coordination Chemistry Reviews*" (2010), Vol. 254, pp. 661-676; Friebe L. et al., "*Advanced Polymer Science*" (2006), Vol. 204, pp. 1-154.

It is further known that the features and applications of the aforementioned stereoregular polymers, in particular of polybutadiene and polyisoprene, vary considerably depending on the microstructure of said polymers. These thus range from the typical elastomeric polymers used for preparing blends for tyre production (i.e. polybutadiene and polyisoprene having a high 1,4-cis content), characterized by extremely low glass transition temperatures ($T_g$) (approximately −110° C. for polybutadiene), to crystalline polymers (i.e. 1,2 syndiotactic polybutadiene and 3,4 syndiotactic polyisoprene), primarily used for the production of shoe soles and characterized by a relatively high melting point ($T_m$) (approximately 220° C. for 1,2 syndiotactic polybutadiene).

Stereospecific polymerization of conjugated dienes using catalytic systems based on transition metals began in 1954, just after the first results obtained in the polymerization of propylene. The first catalytic systems used were obtained by combining titanium tetrachloride ($TiCl_4$) or titanium trichloride ($TiCl_3$) with aluminium alkyls, namely the catalytic systems previously used for polymerizing ethylene or propylene.

The first synthesized stereoregular diene polymer was polyisoprene, having a structure extremely similar to that of natural rubber (namely 1,4-cis structure) described by Horne S. E. et al. in "*Industrial & Engineering Chemistry*" (1956), Vol. 48(4), pp. 784-791, soon to be followed by polyisoprene having a structure analogous to that of gutta-percha (namely 1,4-trans structure) described by Natta G. et al. in "*Chemical Abstract*" (1959), Vol. 53, pp. 3756 and in Italian patent application IT 536631.

By the beginning of the 60s, all stereoisomers of polybutadiene had already been synthesized, namely the 1,4-cis, 1,4-trans, 1,2-syndiotactic and 1,2-isotactic stereoisomers.

Subsequently, various other catalytic systems obtained by combining compounds (e.g., halides, alcoholates, carboxylates) of transition metals [e.g., titanium (Ti), vanadium (V), chromium (Cr), iron (Fe), cobalt (Co), nickel (Ni)], or lanthanides [e.g., neodymium (Nd), praseodymium (Pr), gadolinium (Gd), lanthanum (La)] with suitable alkylating agents [e.g., tri-ethyl-aluminium ($AlEt_3$), di-ethyl-aluminium chloride ($AlEt_2Cl$)] were proposed and studied. It is further known that, of the various polymers obtainable from the stereospecific polymerization of 1,3-butadiene (i.e. 1,4-cis, 1,4-trans, 1,2 syndiotactic, 1,2 isotactic, 1,2 atactic, mixed 1,4-cis/1,2 structure having a variable content of 1,2 units), only 1,4-cis polybutadiene and 1,2 syndiotactic polybutadiene are produced industrially and commercialized.

Polybutadiene having high 1,4-cis content is a synthetic elastomer generally having a content of 1,4-cis units of 96%-97%, a melting point ($T_m$) of approximately −2° C., a crystallization point ($T_c$) of approximately −25° C. and a glass transition temperature ($T_g$) of less than −100° C., the properties of which are very similar to those of natural rubber, and the primary use of which is in the production of elastomeric blends, in particular elastomeric blends for the production of tyres for automobiles and/or lorries. In particular, in tyre production, polybutadiene having a high content of 1,4-cis units is used. Generally, the 1,4-cis polybutadiene is prepared by polymerization processes which use various catalytic systems based on titanium (Ti), cobalt (Co), nickel (Ni), neodymium (Nd).

1,2 syndiotactic polybutadiene is a poorly soluble crystalline polymer, having a melting point ranging from 200° C. to 220° C. which varies depending on the level of syndiotacticity (in other words on the percentage of syndiotactic pentads contained therein), and is generally used for producing transparent films, hoses, in particular for producing shoe soles.

There are thus many catalytic systems used in the polymerization of 1,3-butadiene.

For example, vanadium-based (V) catalytic systems are known in the field of polymerization of conjugated dienes for the ability thereof to provide polymers having a 1,4-trans structure, and are by far the most important systems for the preparation of 1,4-trans polybutadiene. Further details regarding said catalytic systems may be found, for example, in: Porri L. et al., "*Comprehensive Polymer Science*" (1989), Eastmond G. C. et al. Eds., Pergamon Press, Oxford, UK, Vol. 4, Part II, pp. 53-108, cited above.

Heterogeneous catalytic systems obtained by combining vanadium halides [e.g., vanadium trichloride ($VCl_3$), vanadium tetrachloride ($VCl_4$)] with aluminium alkyls [e.g., tri-ethyl-aluminium ($AlEt_3$), di-ethyl-aluminium chloride ($AlEt_2Cl$)] provide a high-molecular-weight, crystalline 1,4-trans polybutadiene (1,4-trans content of 97%-100%), having a melting point ($T_m$) of approximately 145° C. Further details regarding said catalytic systems may be found, for example, in: Natta G. et al., "*La Chimica e L'Industria*" (1959), Vol. 40, p. 362 and "*Chemical Abstract*" (1959), Vol. 53, p. 195; Natta G. et al., "*La Chimica e L'Industria*" (1959), Vol. 41, p. 116 and "*Chemical Abstract*" (1959), Vol. 53, p. 15619.

Polybutadiene having a high content of 1,4-trans units but having lower molecular weight may be prepared using homogeneous catalytic systems such as, for example, vanadium(III)chloride(tris-tetrahydrofuran)/di-ethyl-aluminium chloride ($VCl_3(THF)_3$/$AlEt_2Cl$), vanadium(III)acetylacetonate/di-ethyl-aluminium chloride [$V(acac)_3$/$AlEt_2Cl$] and vanadium(III)acetylacetonate/methylaluminoxane [$V(acac)_3$/MAO]. Further details regarding said catalytic systems may be found, for example, in: Ricci G. et al., "*Polymer Communication*" (1991), Vol. 32, pp. 514-517; Ricci G. et al., "*Journal of Polymer Science Part A: Polymer Chemistry*" (2007), Vol. 45, pp. 4635-4646; Natta G. et al., "*Atti Accademia Nazionale dei Lincei—Classe di Scienze fisiche, matematiche e naturali*" (1961), Vol. 31(5), p. 189 and "*Chemical Abstract*" (1962), Vol. 57, p. 4848; Porri L. et al., "*Die Makromolekulare Chemie*" (1963), Vol. 61(1), pp. 90-103.

Some of the aforementioned homogeneous catalytic systems, for example vanadium(III)acetylacetonate/tri-ethyl-aluminium [$V(acac)_3$/$AlEt_3$], are of some interest for the preparation of 1,2 polybutadiene, as described for example in Natta G. et al., "*La Chimica e L'Industria*" (1959), Vol. 41, p. 526 and "*Chemical Abstract*" (1960), Vol. 54, p. 1258.

Catalytic systems obtained by combining cyclopentadienyl derivatives of vanadium such as, for example, bis(cyclopentadienyl)vanadium chloride ($Cp_2VCl$) and methylcyclopentadienyl vanadium diclhoride bis-triethylphosphine [$(C_5H_4Me)VCl_2(PEt_3)_2$], are able to provide a polybutadiene having a predominantly 1,4-cis structure (content of 1,4-cis units approximately 85%). Further details regarding said catalytic systems may be found for example in: Porri L. et al., "*Metalorganic Catalyst for Synthesis and Polymerization*" (1999), Kaminsky W. Ed., Springer-Verlag Berlin Heidelberg, pp. 519-530; Porri L. et al., "*Metallocene-Based Polyolefins*" (2000), Scheirs J. et al. Eds., John Wiley & Sons Ltd., pp. 115-141; Natta G. et al., "*Atti Accademia Nazionale dei Lincei—Classe di Scienze fisiche, matematiche e naturali*" (1961), Vol. 31(5), p. 189 and "*Chemical Abstract*" (1962), Vol. 57, p. 4848; Porri L. et al., "*Die Makromolekulare Chemie*" (1963), Vol. 61(1), pp. 90-103.

Chromium-based catalytic systems play a significant role in the field of polymerization of conjugated dienes, having been among the first catalytic systems capable of providing polybutadiene having a 1,2 structure. For example, the catalytic systems obtained by combining a soluble chromium compound such as, for example, chromium(III)acetylacetonate [$Cr(acac)_3$] or chromium pentacarbonyl pyridine [$Cr(CO)_5pyridine$] with an aluminium alkyl [e.g., tri-ethyl-aluminium ($AlEt_3$)], have made it possible to obtain 1,2 polybutadiene having an iso- or syndiotactic structure depending on the Al/Cr molar ratio used: syndiotactic at a low Al/Cr ratio, i.e. at a ratio ranging from 2 to 6, isotactic at a high Al/Cr ratio, i.e. at a ratio ranging from 6 to 10, as described, for example, in Natta G. et al., "*La Chimica e L'Industria*" (1959), Vol. 41, p. 1163. It is significant, and confirms their importance, that until isotatic 1,2 polybutadiene has only been obtained using chromium-based catalytic systems.

In more recent years, new, more active and stereospecific catalytic systems have been developed by combining various complexes of chromium (II) [Cr(II)] with bidentate phosphinic ligands and methylaluminoxane (MAO) as described, for example, in: Ricci G. et al., "*Chromium: Environmental, Medical and Material Studies*" (2011), Salden M. P. Ed., Nova Science Publishers Inc., USA, pp. 121-140; Ricci G. et al., "*Macromolecules*" (2001), Vol. 34, pp. 5766-5769; Ricci G. et al., "*Polymer Bullettin*" (2002), Vol. 48, pp. 25-31; Ricci G. et al., "*Organometallics*" (2004), Vol. 23(15), pp. 3727-3732; Ricci G. et al., "*Journal of Molecular Catalysis A: Chemical*" (2007), Vol. 267, pp. 102-107; Ricci G. et al., "*Macromolecular Symposia*" (2004), Vol. 260(1), pp. 172-178. Said catalytic systems have made it possible to obtain 1,2 polybutadiene having a content of 1,2 units of up to 95%, having differing tacticity, namely iso- or syndiotactic, depending on the type of phosphine coordinated to the chromium atom. In particular, predominantly isotactic polymers have been obtained using less sterically hindered phosphines [e.g., bis(dimethylphosphine)methane (dmpm), bis(diphenylphosphine)methane (dppm)], whilst the use of more sterically hindered phosphines [e.g., 1,2-bis(dimethylphosphine)ethane (dmpe), 1,2-bis(diethylphosphine)ethane (depe), bis(diphenylphosphine)amine (dppa), 1,2-bis(diphenylphosphine)ethane (dppe)] has made it possible to synthesize highly syndiotactic 1,2 polybutadiene.

Meanwhile, by contrast with other transition metals such as titanium (Ti), vanadium (V), chromium (Cr), cobalt (Co) and nickel (Ni), iron-based (Fe) catalytic systems have been studied relatively little. Nevertheless, extremely active catalytic systems have been obtained, even if they are not distinguished by a high stereospecificity. This is the case, for example, for catalytic systems based on complexes of iron dichloride or of iron diethyl with aromatic amines (for example phenanthroline, bipyridine) and aluminium alkyls [e.g., tri-iso-butyl-aluminium ($Al(^iBu)_3$), tri-ethyl-aluminium ($AlEt_3$), methylaluminoxane (MAO)], which provide, through the polymerization of 1,3-butadiene, a predominantly 1,2 polybutadiene (~70%; the remaining units are of 1,4-cis type), with complete conversion of the monomer (i.e. 1,3-butadiene) in very short times. Further details regarding said catalytic systems may be found, for example, in: Bazzini C. et al., "*Macromolecular Rapid Communica-* tions" (2002), Vol. 23(15), pp. 922-927; Ricci G. et al., "Journal of Molecular Catalysis A: Chemical" (2003), Vol. 204-205, pp. 287-293; Bazzini C. et al., "Polymer" (2004), Vol. 45, pp. 2871-2875; Ricci G. et al., "Ferrocenes: Compounds, Properties and Applications" (2011), Phillips E. S. Ed., Nova Science Publishers Inc., USA, pp. 273-314.

Cobalt-based catalytic systems are probably the most versatile catalytic systems of the various catalytic systems based on transition metals for the polymerization of conjugated dienes, since with suitable variation in the catalytic formulation thereof they are capable of providing, whilst exhibiting high activity and stereospecificity, all possible stereoisomers of 1,3-butadiene: 1,4-cis polybutadiene, 1,2 polybutadiene, polybutadiene having a mixed 1,4-cis/1,2 structure, 1,4 trans polybutadiene. Further details regarding said stereospecific polymerization may be found, for example, in: Porri L. et al., "Comprehensive Polymer Science" (1989), Eastmond G. C. et al. Eds., Pergamon Press, Oxford, UK, Vol. 4, Part II, pp. 53-108; Thiele S. K. H. et al., "Macromolecular Science. Part C: Polymer Reviews" (2003), C43, pp. 581-628; Osakada K. et al., "Advanced Polymer Science" (2004), Vol. 171, pp. 137-194; Ricci G. et al., "Advances in Organometallic Chemistry Research" (2007), Yamamoto K. Ed., Nova Science Publishers, Inc., USA, pp. 1-36; Ricci G. et al., "Coordination Chemistry Reviews" (2010), Vol. 254, pp. 661-676; cited above; and in Ricci G. et al., "Cobalt: Characteristics, Compounds, and Applications" (2011), Lucas J. Vidmar Ed., Nova Science Publishers, Inc., USA, pp. 39-81.

Cobalt(II)acetylacetonate/di-ethyl-aluminium chloride/water [$Co(acac)_2$/$AlEt_2Cl$/$H_2O$] and cobalt(III)acetylacetonate/tri-ethyl-aluminium/water/carbon sulphide [$Co(acac)_3$/$AlEt_3$/$H_2O$/$CS_2$] catalytic systems, are still used for the industrial production of 1,4-cis polybutadiene and syndiotactic 1,2 polybutadiene, respectively.

In the last few years, new catalytic systems have been obtained by combining cobalt dichloride ($CoCl_2$) complexes with phosphinic ligands as described, for example, in: Ricci G. et al., "Journal of Molecular Catalysis A: Chemical" (2005), Vol. 226, pp. 235-241; Ricci G. et al., "Macromolecules" (2005), Vol. 38, pp. 1064-1070; Ricci G. et al., "Journal of Organometallic Chemistry" (2005), Vol. 690, pp. 1845-1854; Takeuchi M. et al., "Polymer International" (1992), Vol. 29, pp. 209-212; Takeuchi M. et al., "Polymer International" (1995), Vol. 36, pp. 41-45; Takeuchi M. et al., "Macromolecular Chemistry and Physics" (1996), Vol. 197, pp. 729-743.

The peculiarity of the aforementioned new catalytic systems is that they make it possible to obtain polybutadiene having a controlled microstructure (1,4-cis, 1,2, mixed 1,4-cis/1,2 structure) by varying the type of ligand coordinated to the cobalt. For example, polybutadiene having a high content of 1,4-cis units has been obtained in the case of hindered aliphatic phosphines [e.g., tri-tert-butyl phosphine ($P^tBu_3$), tri-iso-propyl phosphine ($P^iPr_3$)], whilst polybutadiene having a mixed 1,4-cis/1,2 structure has been obtained using aliphatic phosphines having lower steric hindrance [e.g., triethyl phosphine ($PEt_3$), tri-n-phosphine ($P^nPr_3$)], as described, for example, in Ricci G. et al., "Cobalt: Characteristics, Compounds, and Applications" (2011), Lucas J. Vidmar Ed., Nova Science Publishers, Inc., USA, pp. 39-81; Ricci G. et al, "Journal of Molecular Catalysis A: Chemical" (2005), Vol. 226, pp. 235-241; cited above.

Meanwhile, the use of catalytic systems based on complexes with aromatic phosphines has led to the formation of predominantly 1,2 polybutadiene, having an increasing level of syndiotacticity as the steric hindrance of the phosphine increases.

Various nickel-based catalytic systems have been used over the years for the polymerization of 1,3-butadiene, such as nickel(II)naphthenate/di-ethyl-aluminium chloride/water [$Ni(naphthenate)_2$/$AlEt_2Cl$/$H_2O$], nickel(II)cyclopentadienyl/methylaluminoxane [$NiCp_2$/MAO], nickel(II)acetylacetonate/methylaluminoxane [$Ni(acac)_2$/MAO], as described, for example, in: Porri L. et al., "Comprehensive Polymer Science" (1989), Eastmond G. C. et al. Eds., Pergamon Press, Oxford, UK, Vol. 4, Part II, pp. 53-108; Thiele S. K. H. et al., "Macromolecular Science. Part C: Polymer Reviews" (2003), C43, pp. 581-628; Osakada K. et al., "Advanced Polymer Science" (2004), Vol. 171, pp. 137-194; cited above; and in: Oliva P. et al., "Die Makromolekulare Chemie, Rapid Communications" (1990), Vol. 11(11), pp. 519-524; Sato H. et al., "Bulletin of the Chemical Society of Japan" (1992), Vol. 65, No. 5, pp. 1299-1306; Longo P. et al., "Macromolecular Rapid Communications" (1998), Vol. 19(1), pp. 31-34.

Some of the aforementioned nickel-based catalytic systems have activities and stereospecificities comparable to those of cobalt-based catalytic systems, and are of industrial interest. In particular, the tri-ethyl-aluminium/nickel(II)octanoate/boron trifluoride diethylether [$AlEt_3$/$Ni(octanoate)_2$/$BF_3.OEt_2$] catalytic system is currently used for the industrial production of polybutadiene having a high 1,4-cis content (i.e. a content of 1,4-cis units of 96%-97%), as described, for example, in German patent DE 2,113,527 and in Throckmorton M. C. et al., "Rubber Chemistry and Technology" (1972), Vol. 45, pp. 268-277; Saltman W. et al., "Rubber Chemistry and Technology" (1973), Vol. 46, pp. 1055-1067.

Lanthanide-based catalytic systems are further known for the high specificity thereof in the 1,4-cis polymerization not only of 1,3-butadiene, but also of many other substituted butadienes as described, for example, in Porri L. et al., "Comprehensive Polymer Science" (1989), Eastmond G. C. et al. Eds., Pergamon Press, Oxford, UK, Vol. 4, Part II, pp. 53-108; Osakada K. et al., "Advanced Polymer Science" (2004), Vol. 171, pp. 137-194; Ricci G. et al., "Advances in Organometallic Chemistry Research" (2007), Yamamoto K. Ed., Nova Science Publishers, Inc., USA, pp. 1-36; Ricci G. et al., "Coordination Chemistry Reviews" (2010), Vol. 254, pp. 661-676; Friebe L. et al., "Advanced Polymer Science" (2006), Vol. 204, pp. 1-154; cited above.

Catalytic systems based on neodymium (Nd), gadolinium (Gd) and praseodymium (Pr) were studied by Chinese researchers in the early 60s as described, for example, in Hsieh L. et al., "Rubber Chemistry and Technology" (1972), Vol. 45, pp. 268, and were immediately found to have some advantages over other catalytic systems used for the synthesis of 1,4-cis polybutadiene. In particular, said catalytic systems provide polybutadiene having a 1,4-cis structure which is more linear than those obtained using catalytic systems based on cobalt (Co), nickel (Ni) and titanium (Ti), and therefore more suitable for the tyre production, which is by far the most important practical application of 1,4-cis polybutadiene.

The conventional catalytic system comprising neodymium-based compounds is obtained by reacting a neodymium compound such as, for example, neodymium(III) acetylacetonate [$Nd(acac)_3$], neodymium(III) 2-ethyl-hexanoate [$Nd(OCOC_7H_{15})_3$], with a chlorine donor such as, for example, di-ethyl-aluminium chloride ($AlEt_2Cl$), ethyl-aluminium sesquichloride ($Al_2Et_3Cl_3$), tert-butyl chloride, and with an aluminium alkyl, such as tri-iso-butyl aluminium (Al'Bu$_3$), di-iso-butyl aluminium hydride (Al'Bu$_2$H). Said catalytic system is currently used for the industrial production of polybutadiene having a very high 1,4-cis content, i.e. a content of 1,4-cis units of 98%. Further details regarding said catalytic system may be found, for example, in: Friebe L. et al., "*Advanced Polymer Science*" (2006), Vol. 204, pp. 1-154, cited above; Cabassi F. et al., "*Transition Metal Catalyzed Polymerizations*" (1988), Quirk R. P. Ed., Cambridge University Press, MA, USA, p. 655; Ricci G. et al., "*Polymer Communication*" (1987), Vol. 28, p. 223; Wilson D. J. et al., "*Polymer Bulletin*" (1992), Vol. 27, pp. 407-411; Porri L. et al., "*Macromolecular Symposia*" (1998), Vol. 128(1), pp. 53-61; Porri L. et al., "*ACS Symposium Sereies*" (2000), Vol. 749, pp. 15-30.

The titanium(IV)chloride/trialkyl aluminium catalytic system (TiCl$_4$/Al(R)$_3$, in which R may be, for example, methyl, ethyl, iso-butyl, cyclohexyl), was the first catalyst used for the polymerization of 1,3-butadiene as described, for example, in: Porri L. et al., "*Comprehensive Polymer Science*" (1989), Eastmond G. C. et al. Eds., Pergamon Press, Oxford, UK, Vol. 4, Part II, pp. 53-108; Horne S. E. et al., "*Industrial Engineering Chemistry*" (1956), Vol. 48, pp. 784-791; cited above. Depending on the Al/Ti molar ratio, polybutadienes predomininantly having a 1,4-cis structure (i.e. content of 1,4-cis units of 65%-70%), or polybutadienes having a mixed 1,4-cis/1,4-trans structure may be obtained. Polybutadienes having a higher content of 1,4-cis units, of approximately 92%-95%, have been obtained by combining various types of alkyl compounds of aluminium such as, for example, compounds of formula Al(R)$_3$, in which R may be, for example, methyl, ethyl, iso-butyl, cyclohexyl, preferably tri-iso-butyl aluminium [Al('Bu)$_3$], with titanium-based catalytic systems containing iodine (e.g., titanium(IV)iodide (TiI$_4$), titanium diiodide-dichloride (TiCl$_2$I$_2$), titanium iodide trichloride (TiCl$_3$I)] as described, for example, in: Porri L. et al., "*Comprehensive Polymer Science*" (1989), Eastmond G. C. et al. Eds., Pergamon Press, Oxford, UK, Vol. 4, Part II, pp. 53-108, cited above; Cooper W. et al., "*The Stereo Rubbers*" (1997), W. M. Saltman Ed., Wiley, New York, p. 21; Marconi W. et al., "*La Chimica e l'Industria*" (1963), Vol. 45, pp. 522-528; Marconi W. et al., "*Journal of Polymer Science Part A: General Papers*" (1965), Vol. 3(2), pp. 735-752.

Titanium-based catalytic systems were the first ones used for the synthesis of polybutadiene having a high content of 1,4-cis units, and acted as a basis for the development of the processes used industrially for said synthesis both in Europe and in the United States. Nowadays, more active and stereospecific catalytic systems are available, based on other metals such as, for example, cobalt (Co), nickel (Ni) and neodymium (Nd).

However, catalytic systems based on titanium are also capable, with suitable variation of the catalytic formulation, of providing polybutadiene having a 1,2 structure and a 1,4-trans structure. For example, the α-titanium trichloride/tri-ethyl-aluminium (α-TiCl$_3$/AlEt$_3$) catalytic system was the first catalyst used for the preparation of 1,4-trans polybutadiene, as described, for example, in Porri L. et al., "*Comprehensive Polymer Science*" (1989), Eastmond G. C. et al. Eds., Pergamon Press, Oxford, UK, Vol. 4, Part II, pp. 53-108; Natta G. et al. in "*Chemical Abstract*" (1959), Vol. 53, pp. 3756 and in Italian patent application IT 536631; cited above.

By contrast with titanium-based catalytic systems, zirconium-based catalytic systems have been studied much less, likely because they are considered poorly effective for the polymerization of conjugated dienes. Very recently, however, a new catalyst based on a pyridine complex of zirconium, capable of providing a polybutadiene having a high content of 1,4-cis units (i.e. content of 1,4-cis units ≥99.9%), has been described: further details regarding said catalyst may be found in Annunziata L. et al., "*Macromolecules*" (2011), Vol. 44, pp. 1934-1941.

Since the (co)polymers of conjugated dienes, in particular polybutadiene, having a high content of 1,4-trans units can advantageously be used for the production of tyres, in particular for the tread of tyres having good wear resistance, as well as in the footwear industry (for example, in the production of shoe soles), the study of new catalytic systems capable of providing said (co)polymers is still of great interest.

The Applicant has set itself the task of finding a novel complex of zirconium which can be used in a catalytic system capable of providing (co)polymers of conjugated dienes such as, for example, linear or branched polybutadiene, having a high content of 1,4-trans units, i.e. a content of 1,4-trans units ≥94%.

The Applicant has now found a novel pyridine complex of zirconium having general formula (I) as defined below, which is capable of providing (co)polymers of conjugated dienes such as, for example, linear or branched polybutadiene, having a high content of 1,4-trans units, i.e. a content of 1,4-trans units ≥94%.

The present invention therefore relates to a pyridine complex of zirconium having general formula (I):

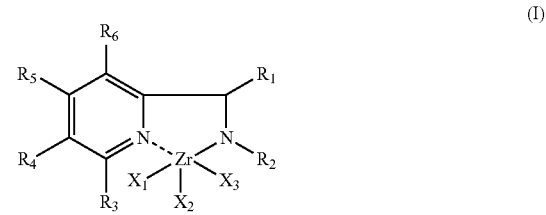

in which:

R$_1$ and R$_2$, identical or different, represent a hydrogen atom; or are selected from linear or branched, optionally halogenated C$_1$-C$_{20}$, preferably C$_1$-C$_{15}$, alkyl groups, optionally substituted cycloalkyl groups, optionally substituted aryl groups;

R$_3$, R$_4$, R$_5$ and R$_6$, identical or different, represent a hydrogen atom; or are selected from linear or branched, optionally halogenated C$_1$-C$_{20}$, preferably C$_1$-C$_{15}$, alkyl groups, optionally substituted cycloalkyl groups, optionally substituted aryl groups, nitro groups, hydroxyl groups, amino groups;

X$_1$, X$_2$ and X$_3$, identical or different, represent a halogen atom such as, for example, chlorine, bromine, iodine, preferably chlorine; or are selected from linear or branched C$_1$-C$_{20}$, preferably C$_1$-C$_{15}$, alkyl groups, —OCOR$_7$ groups or —OR$_7$ groups in which R$_7$ is selected from linear or branched C$_1$-C$_{20}$, preferably C$_1$-C$_{15}$, alkyl groups; or one of X$_1$, X$_2$ and X$_3$ represents a group having general formula (II):

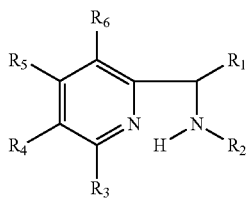

in which $R_1$, $R_2$, $R_3$, $R_4$, $R_5$ and $R_6$, have the same meanings described above.

For the purpose of the present description and of the following claims, the definitions of numerical ranges always include the endpoints unless stated otherwise.

For the purpose of the present description and of the following claims, the term "comprising" also includes the terms "substantially consisting of" or "consisting of".

The term "$C_1$-$C_{20}$ alkyl groups" refers to linear or branched alkyl groups having from 1 to 20 carbon atoms. Specific examples of $C_1$-$C_{20}$ alkyl groups are: methyl, ethyl, n-propyl, iso-propyl, n-butyl, s-butyl, iso-butyl, tert-butyl, pentyl, hexyl, heptyl, octyl, n-nonyl, n-decyl, 2-butyloctyl, 5-methylhexyl, 4-ethylhexyl, 2-ethylheptyl, 2-ethylhexyl.

The term "optionally halogenated $C_1$-$C_{20}$ alkyl groups" refers to linear or branched, saturated or unsaturated alkyl groups having from 1 to 20 carbon atoms, in which at least one of the hydrogen atoms is substituted with a halogen atom such as, for example, fluorine, chlorine, bromine, preferably fluorine, chlorine. Specific examples of $C_1$-$C_{20}$ alkyl groups optionally halogenated: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluorooctyl, perfluorodecyl.

The term "cycloalkyl groups" refers to cycloalkyl groups having from 3 to 30 carbon atoms. Said cycloalkyl groups may optionally be substituted with one or more groups, identical or different, selected from: halogen atoms; hydroxyl groups; $C_1$-$C_{12}$ alkyl groups; $C_1$-$C_{12}$ alkoxyl groups; cyano groups; amino groups; nitro groups. Specific examples of cycloaklyl groups are: cyclopropyl, 2,2-difluorocyclopropyl, cyclobutyl, cyclopentyl, cyclohexyl, hexamethylcyclohexyl, pentamethylcyclopentyl, 2-cyclooctylethyl, methylcyclohexyl, methoxycyclohexyl, fluorocyclohexyl, phenylcyclohexyl.

The term "aryl groups" refers to aromatic carbocyclic groups. Said aromatic carbocyclic groups may optionally be substituted with one or more groups, identical or different, selected from: halogen atoms such as, for example, fluorine, chlorine, bromine; hydroxyl groups; $C_1$-$C_{12}$ alkyl groups; $C_1$-$C_{12}$ alkoxyl groups; cyano groups; amine groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene.

In a preferred embodiment of the present invention, in said pyridine complex of zirconium having general formula (I):

$R_1$ and $R_2$, identical or different, represent a hydrogen atom; or are selected from $C_1$-$C_{20}$ alkyl groups, preferably are methyl, optionally substituted aryl groups, preferably are phenyl, or phenyl substituted with one or more methyl, iso-propyl, tert-butyl groups; preferably $R_1$ is a hydrogen atom or a methyl and $R_2$ a phenyl, or a phenyl substituted with one or more methyl, iso-propyl, tert-butyl groups;

$R_3$, $R_4$, $R_5$ and $R_6$, identical to each other, represent a hydrogen atom;

$X_1$, $X_2$ and $X_3$, identical or different, represent a halogen atom such as, for example, chlorine, bromine, iodine, preferably chlorine; or one of $X_1$, $X_2$ and $X_3$ represents a group having general formula (II):

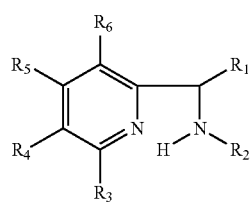

in which $R_1$, $R_2$, $R_3$, $R_4$, $R_5$ and $R_6$, have the same meanings described above.

According to the present invention, the pyridine complex of zirconium having general formula (I) should be understood as being in any physical form such as, for example, the isolated and purified solid form, the solvated form with a suitable solvent, or the form supported on suitable organic or inorganic solids, preferably having a granulated or powdered physical form.

The pyridine complex of zirconium having general formula (I) is prepared from ligands having general formula (III):

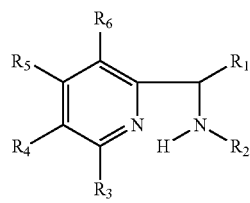

in which $R_1$, $R_2$, $R_3$, $R_4$, $R_5$ and $R_6$ have the same meanings described above.

Specific examples of ligands useful for the purpose of the present invention are those having the following formulae (L1)-(L7):

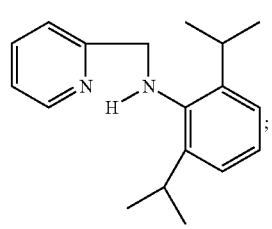

(L2) 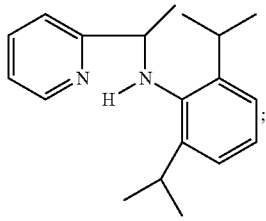

(L3) 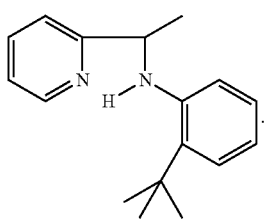

(L4) 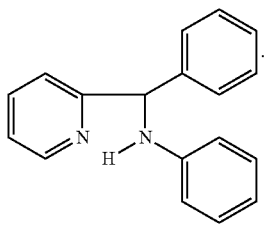

(L5) 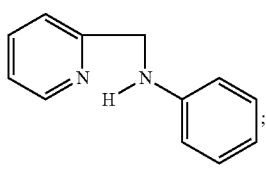

(L6) 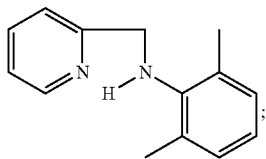

(L7) 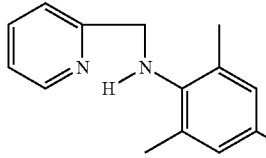

Said ligands having formulae (L1)-(L7) can be prepared by processes known in the art. For example, said ligands having formulae (L1)-(L7) can be prepared by a process comprising: (1) condensation reactions between a suitable aniline and 2-pyridincarboxyaldehyde or 2-acetylpyridine, with formation of the corresponding imine as described, for example, in: Wu J. et al., "*Journal of American Chemistry Society*" (2009), Vol. 131(36), pp. 12915-12917; Laine V. T. et al., "*European Journal of Inorganic Chemistry*" (1999), Vol. 6, pp. 959-964; Bianchini C. et al., "*New Journal of Chemistry*" (2002), Vol. 26(4), pp. 387-397; Lai Yi-C. et al., "*Tetrahedron*" (2005), Vol. 61(40), pp. 9484-9489; (2) transformation of the synthesized imine into the corresponding amine as described, for example, in: Nienkemper K. et al., "*Journal of Organometallic Chemistry*" (2008), Vol. 693(8-9), pp. 1572-1589; Lin Y. et al., "*Dalton Transactions*" (2012), Vol. 41(22), pp. 6661-6670.

The pyridine complex of zirconium having general formula (I) may be prepared by processes known in the art. For example, said pyridine complex of zirconium may be prepared by a reaction between zirconium compounds having general formula $Zr(X)_4$ in which X is a halogen atom such as, for example, chlorine, bromine, iodine, preferably chlorine, as such or complexed with ethers [for example, diethylether, tetrahydrofuran (THF), dimethoxyethane], with ligands having formulae (L1)-(L7) as stated above, said ligands being used in a stoichiometric amount, working, preferably, in the presence of at least one solvent, which may be selected, for example, from: chlorinated solvents (for example, methylene chloride), etheric solvents [for example, tetrahydrofuran (THF)], hydrocarbon solvents (for example, toluene), or mixtures thereof, at a temperature ranging from 25° C. to 110° C., preferably at the reflux temperature of the solvent. Otherwise, if one of $X_1$, $X_2$ and $X_3$ represents a groups having general formula (II)

(II) 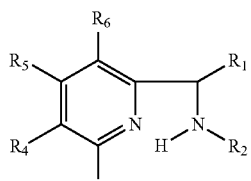

in which $R_1$, $R_2$, $R_3$, $R_4$, $R_5$ and $R_6$ have the same meanings described above, said ligands, before being reacted with the aforementioned zirconium compounds, are reacted with an alkyl lithium such as, for example, lithium n-butyl (n-BuLi), to obtain a salt of said ligands which is subsequently reacted with the aforementioned zirconium compounds working as described above. The pyridine complex of zirconium thus obtained can subsequently be recovered by methods known in the art such as, for example, precipitation using a non-solvent (for example, pentane), followed by separation by filtering or decanting and optional subsequent solubilization in a suitable solvent, followed by low-temperature crystallization.

For the purpose of the present description and of the following claims, the phrase "room temperature" refers to a temperature ranging from 20° C. to 25° C.

As stated previously, the present invention further relates to a catalytic system for the (co)polymerization of conjugated dienes comprising said pyridine complex of zirconium having general formula (I).

The present invention therefore further relates to a catalytic system for the (co)polymerization of conjugated dienes comprising:

(a) at least one pyridine complex of zirconium having general formula (I);
(b) at least one co-catalyst selected from organic compounds of an element M' different from carbon, said element M' being selected from elements belonging to groups 2, 12, 13, or 14, of the Periodic Table of the Elements, preferably from: boron, aluminium, zinc, magnesium, gallium, tin, still more preferably from aluminium, boron.

In general, the formation of the catalytic system comprising the pyridine complex of zirconium having general formula (I) and the co-catalyst (b) is preferably carried out in an inert liquid medium, more preferably in a hydrocarbon solvent. The selection of the pyridine complex of zirconium having general formula (I) and of the co-catalyst (b), as well as the particular methodology used, may vary depending on the molecular structures and on the desired result, as similarly reported in the related literature available to the person skilled in the art for other complexes of transition metals with imine ligands, such as, for example, reported by L. K. Johnson et al., in "Journal of the American Chemical Society" (1995), Vol. 117, pp. 6414-6415, and by G. van Koten et al., in "Advances in Organometallic Chemistry" (1982), Vol. 21, pp. 151-239.

In a further preferred embodiment of the present invention, said co-catalyst (b) may be selected from ($b_1$) aluminium alkyls having general formula (IV):

$$Al(X')_n(R_8)_{3-n} \tag{IV}$$

in which X' represents a halogen atom such as, for example, chlorine, bromine, iodine, fluorine; $R_8$ is selected from linear or branched $C_1$-$C_{20}$ alkyl groups, cycloalkyl groups, aryl groups, said groups being optionally substituted with one or more atoms of silicon or germanium; and n is an integer ranging from 0 to 2.

In a further preferred embodiment of the present invention, said co-catalyst (b) may be selected from ($b_2$) organo-oxygenated compounds of an element M' different from carbon belonging to groups 13 or 14 of the Periodic Table of the Elements, preferably organo-oxygenated compounds of aluminium, gallium, tin. Said organo-oxygenated compounds ($b_2$) may be defined as organic compounds of M' in which this latter is bonded to at least one oxygen atom and to at least one organic group formed by an alkyl group having from 1 to 6 carbon atoms, preferably methyl.

In a further preferred embodiment of the present invention, said co-catalyst (b) may be selected from ($b_3$) compounds or mixtures of organometallic compounds of an element M' different from carbon capable of reacting with the pyridine complex of zirconium having general formula (I), extracting from this a σ-linked substituent $X_1$, $X_2$ or $X_3$, to form on the one hand at least one neutral compound, and on the other a ionic compound consisting of a cation containing the metal (Zr) coordinated by the ligand, and of a non-coordinating organic anion containing the metal M', whose negative charge is delocalized on a multicentric structure.

It should be noted that for the purpose of the present invention and of the following claims the term "Periodic Table of the Elements" refers to the "IUPAC Periodic Table of the Elements", version dated 22 Jun. 2007, available at the following Internet address: www.iupac.org/fileadmin/user_upload/news/IUPAC_Periodic_Table-1Jun12.pdf.

Specific examples of aluminium alkyls having general formula (IV) which are particularly useful for the purpose of the present invention are: tri-methyl-aluminium, tri-(2,3,3-tri-methyl-butyl)-aluminium, tri-(2,3-di-methyl-hexyl)-aluminium, tri-(2,3-di-methyl-butyl)-aluminium, tri-(2,3-di-methyl-pentyl)-aluminium, tri-(2,3-di-methyl-heptyl)-aluminium, tri-(2-methyl-3-ethyl-pentyl)-aluminium, tri-(2-methyl-3-ethyl-hexyl)-aluminium, tri-(2-methyl-3-ethyl-heptyl)-aluminium, tri-(2-methyl-3-propyl-hexyl)-aluminium, tri-ethyl-aluminium, tri-(2-ethyl-3-methyl-butyl)-aluminium, tri-(2-ethyl-3-methyl-pentyl)-aluminium, tri-(2,3-di-ethyl-pentyl-aluminium), tri-n-propyl-aluminium, tri-iso-propyl-aluminium, tri-(2-propyl-3-methyl-butyl)-aluminium, tri-(2-iso-propyl-3-methyl-butyl)-aluminium, tri-n-butyl-aluminium, tri-iso-butyl-aluminium (TIBA), tri-tert-butyl-aluminium, tri-(2-iso-butyl-3-methyl-pentyl)-aluminium, tri-(2,3,3-tri-methyl-pentyl)-aluminium, tri-(2,3,3-tri-methyl-hexyl)-aluminium, tri-(2-ethyl-3,3-di-methyl-butyl)-aluminium, tri-(2-ethyl-3,3-di-methyl-pentyl)-aluminium, tri-(2-iso-propyl-3,3-dimethyl-butyl)-aluminium, tri-(2-tri-methylsilyl-propyl)-aluminium, tri-2-methyl-3-phenyl-butyl)-aluminium, tri-(2-ethyl-3-phenyl-butyl)-aluminium, tri-(2,3-di-methyl-3-phenyl-butyl)-aluminium, tri-(2-phenyl-propyl)-aluminium, tri-[2-(4-fluoro-phenyl)-propyl]-aluminium, tri-[2-(4-chloro-phenyl)-propyl]-aluminium, tri-[2-(3-iso-propyl-phenyl-tri-(2-phenyl-butyl)-aluminium, tri-(3-methyl-2-phenyl-butyl)-aluminium, tri-(2-phenyl-pentyl)-aluminium, tri-[2-(penta-fluoro-phenyl)-propyl]-aluminium, tri-(2,2-diphenyl-ethyl]-aluminium, tri-(2-phenyl-methyl-propyl)-aluminium, tri-pentyl-aluminium, tri-hexyl-aluminium, tri-cyclohexyl-aluminium, tri-octyl-aluminium, di-ethyl-aluminium hydride, di-n-propyl-aluminium hydride, di-n-butyl-aluminium hydride, di-iso-butyl-aluminium hydride (DIBAH), di-hexyl-aluminium hydride, di-iso-hexyl-aluminium hydride, di-octyl-aluminium hydride, di-iso-octyl-aluminium hydride, ethyl-aluminium dihydride, n-propyl-aluminium dihydride, iso-butyl-aluminium dihydride, di-ethyl-aluminium chloride (DEAC), mono-ethyl-aluminium dichloride (EADC), di-methyl-aluminium chloride, di-iso-butyl-aluminium chloride, iso-butyl-aluminium dichloride, ethyl-aluminium sesquichloride (EASC), as well as the corresponding compounds in which one of the hydrocarbon substituents is substituted by a hydrogen atom and those in which one or two of the hydrocarbon substituents are substituted with an iso-butyl group. Tri-ethyl-aluminium, tri-iso-butyl-aluminium (TIBA), di-iso-butyl-aluminium hydride (DIBAH), are particularly preferred.

Preferably, when used for the formation of a (co)polymerization catalytic system according to the present invention, the aluminium alkyls having general formula (IV) may be placed in contact with a pyridine complex of zirconium having general formula (I), in proportions such that the molar ratio between the zirconium present in the pyridine complex of zirconium having general formula (I) and the aluminium present in the aluminium alkyls having general formula (IV) may range from 5 to 5000, preferably ranges from 10 to 1000. The sequence in which the pyridine complex of zirconium having general formula (I) and the aluminium alkyl having general formula (IV) are placed in contact with one another is not particularly critical.

Further details regarding the aluminium alkyls having general formula (IV) may be found in international patent application WO 2011/061151.

In a particularly preferred embodiment, said organo-oxygenated compounds ($b_2$) may be selected from aluminoxanes having general formula (V):

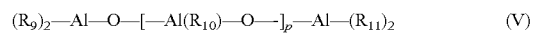
$$(R_9)_2-Al-O-[-Al(R_{10})-O-]_p-Al-(R_{11})_2 \tag{V}$$

in which $R_9$, $R_{10}$ and $R_{11}$, identical or different, represent a hydrogen atom, a halogen atom such as, for example, chlorine, bromine, iodine, fluorine; or are selected from linear or branched $C_1$-$C_{20}$ alkyl groups, cycloalkyl groups, aryl groups, said groups being optionally substituted with one or more atoms of silicon or germanium; and p is an integer ranging from 0 to 1000.

As is known, aluminoxanes are compounds containing Al—O—Al bonds, having a variable O/Al ratio, obtainable by processes known in the art such as, for example, by reacting, in controlled conditions, an aluminium alkyl, or an aluminium alkyl halide, with water or with other compounds containing predetermined amounts of available water as, for example, when aluminium trimethyl is reacted with aluminium sulphate hexahydrate, copper sulphate pentahydrate, or iron sulphate pentahydrate.

Said aluminoxanes and, in particular, the methylaluminoxane (MAO), are compounds obtainable by the known processes of organometallic chemistry such as, for example, by the addition of trimethyl aluminium to a suspension of aluminium sulphate hydrate in hexane.

Preferably, when used for forming a (co)polymerization catalytic system according to the present invention, the aluminoxanes having general formula (V) may be placed in contact with a pyridine complex of zirconium having general formula (I), in proportions such that the molar ratio between the aluminium (Al) present in the aluminoxane having general formula (V) and the zirconium present in the pyridine complex of zirconium having general formula (I) is ranging from 10 to 10000, preferably ranging from 100 to 5000. The sequence in which the pyridine complex of zirconium having general formula (I) and the aluminoxane having general formula (V) are placed in contact with one another is not particularly critical.

As well as the aforementioned preferred aluminoxanes having general formula (V), the definition of compound ($b_2$) according to the present invention also includes the galloxanes, in which gallium takes the place of aluminium in general formula (V), and the stannoxanes, in which tin takes the place of aluminium in general formula (V), the use of which as polymerization co-catalysts for olefins in the presence of metallocene complexes is known.

Further details regarding said galloxanes and stannoxanes may be found, for example, in American patents U.S. Pat. No. 5,128,295 and U.S. Pat. No. 5,258,475.

Specific examples of aluminoxanes having general formula (V) which are particularly useful for the purpose of the present invention are: methylaluminoxane (MAO), ethylaluminoxane, n-butyl-aluminoxane, tetra-iso-butyl-aluminoxane (TIBAO), tert-butyl-aluminoxane, tetra-(2,4,4-tri-methyl-pentyl)-aluminoxane (TIOAO), tetra-(2,3-di-methyl-butyl)-aluminoxane (TDMBAO), tetra-(2,3,3-tri-methyl-butyl)aluminoxane (TTMBAO). Methylaluminoxane (MAO), as such or in dry form (MAO-dry), is particularly preferred.

Further details regarding the aluminoxanes having general formula (V) may be found in international patent application WO 2011/061151.

In a preferred embodiment of the present invention, said compounds or mixtures of compounds ($b_3$) may be selected from organic compounds of aluminium and especially of boron, such as, for example, those represented by the following general formulae:

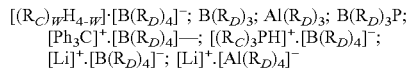

in which w is an integer ranging from 0 to 3, each $R_C$ group independently represents an alkyl group or an aryl group having from 1 to 10 carbon atoms, and each $R_D$ group independently represents a partially or totally, preferably totally, fluorinated aryl group, having from 6 to 20 carbon atoms, P represents an optionally substituted pyrrole radical.

Preferably, when used for forming a (co)polymerization catalytic system according to the present invention, the compounds or mixtures of compounds ($b_3$) may be placed in contact with a pyridine complex of zirconium having general formula (I) in proportions such that the molar ratio between the metal (M') present in the compounds or mixtures of compounds ($b_3$) and the zirconium (Zr) present in the pyridine complex of zirconium having general formula (I) is ranging from 0.1 to 15, preferably ranges from 0.5 to 10, more preferably ranges from 1 to 6. The sequence in which the pyridine complex of zirconium having general formula (I) and the compound or mixture of compounds ($b_3$) are placed in contact with one another is not particularly critical.

Said compounds or mixtures of compounds ($b_3$), especially if $X_1$, $X_2$ and $X_3$ in the pyridine complex of zirconium having general formula (I) are different from alkyl, have to be used in combination with an aluminoxane having general formula (V) such as, for example, methylaluminoxane (MAO) or, preferably, with an aluminium alkyl having general formula (IV), more preferably an aluminium trialkyl having from 1 to 8 carbon atoms in each alkyl residue such as, for example, tri-methyl-aluminium, tri-ethyl-aluminium, tri-iso-butylaluminium (TIBA).

Examples of the methodologies generally used for providing a (co)polymerization catalytic system according to the present invention, if compounds or mixtures of compounds ($b_3$) are used, are qualitatively outlined in the following list, which does not, however, in any way limit the overall scope of the present invention:

($m_1$) contacting a pyridine complex of zirconium having general formula (I), in which at least one of $X_1$, $X_2$ and $X_3$ is an alkyl group, with at least one compound or mixtures of compounds ($b_3$) of which the cation is capable of reacting with said alkyl group to form a neutral compound, and of which the anion is bulky, non-coordinating and capable of delocalizing the negative charge;

($m_2$) reacting a pyridine complex of zirconium having general formula (I) with at least one aluminium alkyl having general formula (IV), preferably an aluminium trialkyl, used in molar excess from 10/1 to 300/1, followed by reacting with strong Lewis acid, such as tris (pentafluorophenyl)boron [compound ($b_3$)], in a virtually stoichiometric amount or in slight excess with respect to the zirconium (Zr);

($m_3$) contacting and reacting a pyridine complex of zirconium having general formula (I) with a molar excess from 10/1 to 1000/1, preferably from 100/1 to 500/1, of at least one aluminium trialkyl or an alkyl aluminium halide which can be represented by the formula $AlR'''_m Z_{3-m}$, in which R''' is a linear or branched $C_1$-$C_8$ alkyl group, or a mixture thereof, Z is a halogen, preferably chlorine or bromine, and m is a decimal number ranging from 1 to 3, followed by adding to the composition thus obtained at least one compound or mixture of compounds ($b_3$) in amounts such that the ratio between said compound or mixture of compounds ($b_3$) or the aluminium of said compound or mixture of compounds ($b_3$) and the zirconium (Zr) of the pyridine complex of zirconium having general formula (I) is ranging from 0.1 to 15, preferably from 1 to 6.

Examples of compounds or mixtures of compounds ($b_3$) capable of producing an ionic catalytic system for reaction with a pyridine complex of zirconium having general formula (I) according to the present invention are described, albeit in relation to the formation of ionic metallocene complexes, in the following publications, the content of which is incorporated herein by reference:

W. Beck et al., "*Chemical Reviews*" (1988), Vol. 88, pp. 1405-1421;

S. H. Stares, "*Chemical Reviews*" (1993), Vol. 93, pp. 927-942;

European patent applications EP 277 003, EP 495 375, EP 520 732, EP 427 697, EP 421 659, EP 418 044, published international patent application WO 92/00333, WO 92/05208.

Specific examples of compounds or mixtures of compounds ($b_3$) particularly useful for the purpose of the present invention are: tributylammonium-tetrakis-pentafluorophenyl-borate, tributylammonium-tetrakis-pentafluorophenyl-aluminate, tributylammonium-tetrakis-[(3,5-di-(trifluoro-phenyl)]-borate, tributylammonium-tetrakis-(4-fluorophenyl)]-borate, N,N-dimethylbenzylammonium-tetrakis-pentafluoro-phenyl-borate, N,N-dimethyl-hexyl-ammonium-tetrakis-pentafluoropenyl-borate, N,N-dimethylanilinium-tetrakis-(pentafluoro-phenyl)-borate, N,N-dimethylanilinium-tetrakis-(pentafluorophenyl)-aluminate, di-(propyl)-ammonium-tetrakis-(pentafluorophenyl)-borate, di-(cyclohexyl)-ammonium-tetrakis-(penta-fluoro-phenyl)-borate, tri-phenyl-carbene-tetrakis-(pentafluorophenyl)-borate, tri-phenylcarbene-tetrakis-(penta-fluorophenyl)-aluminate, tris(pentafluorophenyl) boron, tris(pentafluorophenyl)-aluminium, or mixtures thereof. The tetrakis-pentafluorophenyl-borates are preferred.

For the purpose of the present description and of the following claims, the terms "mole" and "molar ratio" are used both in reference to compounds formed of molecules and in reference to atoms and ions, neglecting the terms gram atom or atomic ratio for the latter even if these terms are more scientifically correct.

For the purpose of the present invention, other additives or components may optionally be added to the aforementioned catalytic system so as to adapt it to meet specific requirements in practice. The catalytic systems thus obtained should thus be considered to be within the scope of the present invention. Additives and/or components which can be added to the preparation and/or to the formulation of the catalytic system according to the present invention are, for example: inert solvents such as, for example, aliphatic and/or aromatic hydrocarbons; aliphatic and/or aromatic ethers; weakly coordinating additives (e.g., Lewis bases) selected, for example, from non-polymerizable olefins; sterically hindered or electron-deficient ethers; halogenating agents such as, for example, silicon halides, halogenated, preferably chlorinated, hydrocarbons; or mixtures thereof.

Said catalytic system may be prepared, as stated previously, by methods known in the art.

For example, said catalytic system may be prepared separately (preformed) and subsequently introduced into the (co)polymerization environment. For this purpose, said catalytic system may be prepared by reacting at least one pyridine complex of zirconium (a) having general formula (I) with at least one co-catalyst (b), optionally in the presence of other additives or components selected from those listed above, in the presence of a solvent such as, for example, toluene, heptane, at a temperature ranging from 20° C. to 60° C., for a time ranging from 10 seconds to 10 hours, preferably ranging from 30 seconds to 5 hours. More details regarding the preparation of said catalytic system may be found in the examples below reported.

Alternatively, said catalytic system may be prepared in situ, i.e. directly in the (co)polymerization environment. For this purpose, said catalytic system may be prepared by separately introducing the pyridine complex of zirconium (a) having general formula (I), the co-catalyst (b) and the preselected conjugated diene(s) to be (co)polymerized, working in the conditions in which the (co)polymerization is carried out.

For the purpose of the present invention, the aforementioned catalytic systems may also be supported on inert solids, preferably formed by silicon and/or aluminium oxides, such as silica, alumina or silico-aluminates. For supporting said catalytic systems, the known supporting methods may be used, including, generally speaking, contact, in a suitable inert liquid medium, between the support, optionally activated by heating to a temperature over 200° C., and one or both of the components (a) and (b) of the catalytic system object of the present invention. It is not necessary, for the purposes of the present invention, for both of the components to be supported, it also being possible for only the pyridine complex of zirconium (a) having general formula (I) or the co-catalyst (b) to be present on the surface of the support. In this latter case, the component absent from the surface is subsequently placed in contact with the supported component at the moment when it is desired to form the active catalyst for the polymerization.

The pyridine complex of zirconium having general formula (I) and the catalytic systems based thereon, which have been supported on a solid by functionalizing said solid and forming a covalent bond between the solid and the pyridine complex of zirconium having general formula (I), are also within the scope of the present invention.

Further, the present invention relates to a process of (co)polymerization of conjugated dienes, characterized by the use of said catalytic system.

The amount of the pyridine of zirconium (a) having general formula (I) and of the co-catalyst (b) which can be used in the (co)polymerization of conjugated dienes varies depending on the (co)polymerization process which it is desired to implement. However, said amount is such as to obtain a molar ratio between the zirconium (Zr) present in the pyridine complex of zirconium having general formula (I) and the metal present in the co-catalyst (b), e.g., the aluminium if the co-catalyst (b) is selected from the aluminium alkyls ($b_1$) or the aluminoxanes ($b_2$), the boron if the co-catalyst (b) is selected from the compounds or mixtures of compounds ($b_3$) having general formula (III), ranging from the values stated above.

Specific examples of conjugated dienes which can be (co)polymerized using the catalytic system according to the present invention are: 1,3-butadiene, 2-methyl-1,3-butadiene (isoprene), 2,3-dimethyl-1,3-butadiene, 1,3-pentadiene, 1,3-hexadiene, cyclo-1,3-hexadiene. 1,3-butadiene is preferred. The aforementioned (co)polymerizable conjugated dienes may be used on their own or in a mixture of two or more dienes. In the latter case, when a mixture of two or more dienes is used, a copolymer will be obtained.

In a particularly preferred embodiment, the invention relates to a process of polymerization of 1,3-butadiene, characterized by the use of said catalytic system.

Generally speaking, said (co)polymerization may be carried out in the presence of a polymerization solvent generally selected from inert organic solvents such as, for example: saturated aliphatic hydrocarbons such as, for example, butane, pentane, hexane, heptane, or mixtures thereof; saturated cyclo-aliphatic hydrocarbons such as, for example, cyclopentane, cyclohexane, cyclohexane, or mixtures thereof; mono-olefins such as, for example, 1-butene, 2-butene, or mixtures thereof; aromatic hydrocarbons such as, for example, benzene, toluene, xylene, or mixtures thereof; halogenated hydrocarbons such as, for example, methylene chloride, chloroform, carbon tetrachloride, trichloroethylene, perchloroethylene, 1,2-dichloroethane, chlorobenzene, bromobenzene, chlorotoluene, or mixtures thereof. Preferably, the (co)polymerization solvent is selected from saturated aliphatic hydrocarbons.

Alternatively, said (co)polymerization may be carried our using the same conjugated diene(s) which is/are to be (co)polymerized as the (co)polymerization solvent, in a process known as a bulk process.

Generally speaking, the concentration of the conjugated diene to be (co)polymerized in said (co)polymerization solvent is ranging from 5% by weight to 50% by weight, preferably ranging from 10% by weight to 20% by weight, with respect to the total weight of the mixture of conjugated diene and inert organic solvent.

Generally speaking, said (co)polymerization may be carried out at a temperature ranging from −70° C. and +100° C., preferably ranging from −20° C. to +80° C.

As regards the pressure, it is preferable to work at the pressure of the components of the mixture which is to be (co)polymerized.

Said (co)polymerization may be carried out either continuously or in batch.

As stated above, said process makes it possible to obtain (co)polymers of conjugated dienes, such as linear or branched polybutadiene, having a high content of 1,4-trans units, i.e. a content of 1,4-trans units ≥94%.

For the purpose of better understanding the present invention and for putting it into practice, some illustrative, non-limiting examples are given in the following.

EXAMPLES

Reagents and Materials

Figure 1:
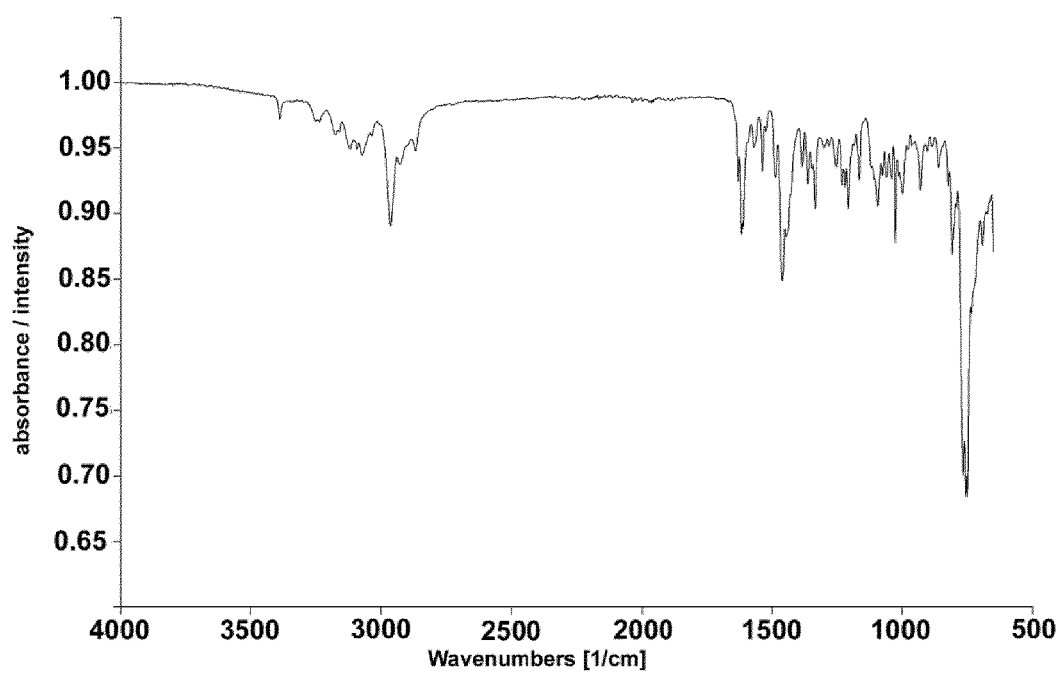
FIG. 1. Illustrated is a FTIR-ATR spectrum of the $ZrCl_3$ (L1) complex obtained from the synthesis described in Example 8.

The following list states the reagents and materials used in the following examples of the invention, any optional pre-treatments thereof, and the manufacturer thereof:

2,6-di-iso-propylaniline (Aldrich): used as such;
2-tert-butylaniline (Aldrich): used as such;
2-benzoylpyridine (Aldrich): used as such;
aniline (Aldrich): distilled at reduced pressure and kept in inert atmosphere;
2,4,6-tri-methylaniline (Aldrich): used as such;
2-pyridincarboxyaldehyde (Aldrich): used as such;
2-acetylpyridine (Aldrich): used as such;
dichloromethane (Carlo Erba, RPE): used as such;
methanol (Carlo Erba, RPE): used as such, or optionally anhydrified by distillation over magnesium (Mg);
sodium boro hydride (Aldrich): used as such;
ethyl acetate (Aldrich): used as such;
hexane (Aldrich): pure, ≥99%, distilled over sodium (Na) in an inert atmosphere;
ethyl ether (Aldrich): used as such;
formic acid (Aldrich): used as such;
heptane (Aldrich): pure, ≥99%, distilled over sodium (Na) in an inert atmosphere;
sodium sulphate (Aldrich): used as such;
chloroform (Aldrich): used as such;
toluene (Aldrich): pure, ≥99.5%, distilled over sodium (Na) in an inert atmosphere;
zirconium tetrachloride ($ZrCl_4$) (Stream Chemicals): used as such;
zirconium tetrachloride:tetrahydrofuran complex (1:2) [$ZrCl_4(THF)_2$] (Aldrich): used as such;
tetrahydrofuran (THF) (Carlo Erba, RPE): kept under reflux over potassium/benzophenone and then distilled under nitrogen;
lithium n-butyl (Aldrich): used as such;
1,3-butadiene (Air Liquide): pure, ≥99.5%, evaporated from the container prior to any production, dried by passing through a column packed with molecular sieves, and condensed within the reactor which has been pre-cooled to −20° C.;
methylaluminoxane (MAO) (toluene solution at 10% by weight) (Aldrich): used as such, or in dry form (MAO-dry) obtained by removing the free tri-methyl-aluminium together with the solvent from the toluene solution under vacuum and drying the residue obtained still under vacuum;
hydrochloric acid in aqueous solution at 37% (Aldrich): used as such;
tri-iso-butyl-aluminium (TIBA) (Aldrich): used as such;
deuterated tetrachloroethylene ($C_2D_2Cl_4$) (Acros): used as such;
deuterated chloroform ($CDCl_3$) (Acros): used as such.

The following analysis and characterization methodologies were used.

Elemental Analysis a) Zr Determination

To determine the amount of zirconium (Zr) by weight in the pyridine complexes of zirconium used for the purpose of the present invention, an exactly weighed aliquot, working in a dry box under nitrogen flow, of approximately 30 mg-50 mg of sample, was placed in a platinum crucible of approximately 30 ml, together with a mixture of 1 ml of 40% hydrofluoric acid (HF), 0.25 ml of 96% sulphuric acid ($H_2SO_4$), and 1 ml of 70% nitric acid ($HNO_3$). The crucible was subsequently heated on a plate, increasing the temperature until white sulphur fumes appeared (approximately 200° C.). The mixture thus obtained was cooled to room temperature (20° C.-25° C.), 1 ml of 70% nitric acid ($HNO_3$) was added, and was then brought back to the point where fumes appeared. After the sequence was repeated two more times, a clear and almost colourless solution was obtained. Subsequently, in the cold, 1 ml of nitric acid ($HNO_3$) and approximately 15 ml of water were added, whilst heating to 80° C., for approximately 30 minutes. The sample thus prepared was diluted with Milli-Q-purity water up to a weight of approximately 50 g, exactly weight, to obtain a solution on which the instrumental analytic determination was carried out using a Thermo Optek IRIS Advantage Duo ICP-OES (optical emission plasma) spectrometer, by comparison with solutions of known concentration. For this purpose, for each analyte, a calibration curve was prepared in the range 0 ppm-10 ppm by measuring solutions of a known titre obtained by dilution by weight of certified solutions.

The solution of the sample prepared as above was further diluted by weight so as to obtain concentrations close to the reference concentrations, before carrying out the spectrophotometry detection. All of the samples were prepared in duplicate. The results were considered acceptable if the individual data of the duplicate tests differed by no more than 2% from the average value thereof.

b) Chlorine Determination

For this purpose, samples of the pyridine complexes of zirconium used for the purpose of the present invention, approximately 30 mg-50 mg, were weighed exactly in 100 ml glass beakers in a dry box under nitrogen flow. 2 g of sodium carbonate ($Na_2CO_3$) were added and, outside the dry box, 50 ml of Mili-Q water. This was brought to boiling on a plate, under magnetic stirring, for approximately 30 minutes. It was left to cool, ⅕ dilute sulphuric acid ($H_2SO_4$) was added, until an acidic reaction, and titration was carried out using silver nitrate ($AgNO_3$) 0.1 N with potentiometric titrator.

c) Carbon, Hydrogen and Nitrogen Determination

The carbon, hydrogen and nitrogen were determined, in the pyridine complexes of zirconium used for the purpose of the present invention, as well as in the ligands used for the purpose of the present invention, using an automatic Carlo Erba 1106 analyser.

$^{13}$C-HMR and $^1$H-HMR Spectra

The $^{13}$C-HMR and $^1$H-HMR spectra were recorded using a Bruker Avance 400 nuclear magnetic resonance spectrometer, using deuterated tetrachloroethylene ($C_2D_2Cl_4$) at 103 C, and hexamethyldisiloxane (HDMS) as an internal standard, or using deuterated chloroform ($CDCl_3$), at 25° C., and tetramethylsilane (TMS) as an internal standard. For this purpose, polymer solutions having concentrations of 10% by weight with respect to the total weight of the polymer solution were used.

The microstructure of the polymers [i.e. content of 1,4-trans units (%)] was determined by analysing the aforementioned spectra on the basis of what is reported in literature by Mochel, V. D., in "*Journal of Polymer Science Part A-1: Polymer Chemistry*" (1972), Vol. 10, Issue 4, pp. 1009-1018.

FTIR-ATR Spectra

The FTIR-ATR spectra were recorded using a Bruker IFS 48 spectrophotometer, equipped with a Thermo Spectra-Tech horizontal ATR connection. The section in which the samples to be analysed are placed is a Fresnel ATR accessory (Shelton, Conn., USA) which uses zirconium selenide crystals (ZnSe) with an angle of incidence of 45° in a horizontal direction. The FTIR-ATR spectra of the pyridine complexes of zirconium used in the present invention were obtained by inserting samples of the pyridine complex of zirconium to be analysed into said section.

FT-IR Spectra

The FT-IR spectra were recorded using Thermo Nicolet Nexus 670 and Bruker IFS 48 spectrophometers.

The FT-IR spectra of the polymers were obtained from polymer films on potassium bromide (KBr) tablets, said film being obtained by depositing a solution of the polymer to be analysed in hot o-dichlorobenzene. The concentration of the polymer solutions analysed was 10% by weight with respect to the total weight of the polymer solution.

Thermal Analysis (DSC)

DSC (Differential Scanning calorimetry) thermal analysis, for the purpose of determining the melting point ($T_m$) and the crystallization temperature ($T_c$) of the polymers obtained, was carried out using a Perkin Elmer Pyris differential scanning calorimeter. For this purpose, 5 mg of polymer were analysed at a scanning speed ranging from 1° C./min to 20 C/min, in an inert nitrogen atmosphere.

Molecular Weight Determination

The molecular weight (MW) of the polymers obtained was carried out by GPC (Gel Permeation Chromatography), working at the following conditions:

Agilent 1100 pump;

Agilent 1100 I.R. detector;

Mixed-A PL column solvent/eluent: tetrahydrofuran (THF);

flow rate: 1 ml/min;

temperature: 25° C.

calculation of molecular mass: Universal Calibration method.

The weight-average molecular weight ($M_w$) and the polydispersion index (PDI) corresponding to the ratio $M_w/M_n$ ($M_n$=number-average molecular weight) are given.

Gas Chromatography-Mass Spectrometry (GC-MS)

Gas chromatography-mass spectrometry (GC-MS) was carried out using a Thermo ISQ single-quadrupole mass spectrometer. For this purpose, samples of the ligands to be analysed were solubilized in methylene chloride ($CH_2Cl_2$) at a concentration of 0.1 mg/ml and were analysed using said spectrometer, working in the following conditions:

means of ionization: Electronic Ionization (EI);

GC ramp: 50° C. per 2 min.; heating at a rate of 10° C./min up to 300° C.;

injector temperature: 300° C.;

injection volume: 1.30 µl;

"transfer line" temperature: 280° C.;

ion source temperature: 250° C.;

quadropole scanning parameters: 35 amu-500 amu with a scanning time of 0.2 s.

Example 1

Synthesis of the Ligand Having Formula (L1)

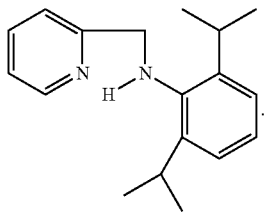

(L1)

1.1 Synthesis of the Compound Having Formula (L1a)

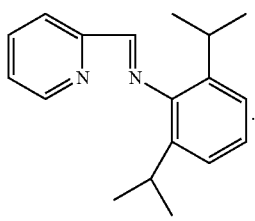

(L1a)

In a 500 ml flask, provided with a Dean-Stark trap for azeotropic water removal, to a solution of 2,6-di-iso-propylaniline (27.93 g, 157.5 mmol) in dichloromethane (300 ml), was added 2-pyridinecarboxyaldehyde (16.86 g, 157.5 mmol). The mixture obtained was heated under reflux for 20 hours and subsequently dried under vacuum, to obtain 41.7 g of a yellow solid (yield=99%) corresponding to the compound having formula (L1a).

Elemental analysis [found (calculated)]: C: 81.14% (81.16%); H: 8.33% (8.32%); N: 10.6% (10.52%).

$^1$H-NMR (CDCl$_3$, δ ppm): 8.72 (d, 1H, PyH), 8.32 (s, 1H CH=N), 8.27 (d, 1H PyH), 7.86 (t, 1H PyH), 7.39 (m, 1H PyH), 7.11-7.20 (m, 3H ArH), 3.00 (sept, 2H CHMe$_2$), 1.18 (d, 12H C(CH$_3$)$_2$).

1.2 Synthesis of the Ligand Having Formula (L1)

Into a 2 liter reactor, provided with a stirrer, were loaded 28 g (105.1 mmol) of the compound having formula (L1a) obtained as described above and 1800 ml of anhydrous methanol: the whole was cooled to 0° C. and subsequently sodium boron hydride (70 g, 1850 mmol) was added in small portions. The mixture obtained was left, under stirring, at room temperature, overnight, and subsequently quenched with brine and extracted using ethyl acetate. The solvent was subsequently removed by distillation at reduced pressure, and the residue obtained was purified by elution in a silica gel chromatography column [eluent: hexane/ethyl acetate mixture in 9/1 ratio (v/v)], and subsequently treated with cold ethyl ether, to obtain 16.9 g of a white crystalline solid (yield=60%) corresponding to the ligand having formula (L1).

GC-MS: M$^+$=m/z 268; [M-C$_3$H$_7$]$^+$=m/z 225; [M-C$_6$H$_6$N]$^+$=m/z 176; m/z 93 C$_6$H$_7$N.

$^1$H-NMR (CDCl$_3$, δ ppm): 8.61 (d, 1H, o-PyH), 7.66 (td, 1H, PyH), 7.30 (d, 1H, PyH), 7.21 (m, 1H, PyH), 7.04-7.12 (m, 3H, ArH), 4.20 (s, 2H, CH$_2$), 4.10 (s, 1H, NH), 3.47 (m, 2H, —CH(CH$_3$)$_2$), 1.42 (d, 12H, —CH(CH$_3$)$_2$).

Example 2

Synthesis of the Ligand Having Formula (L2)

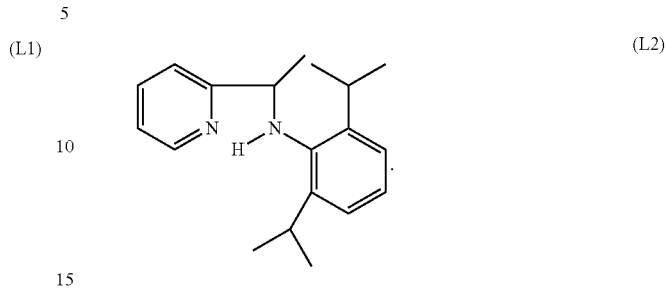

(L2)

2.1 Synthesis of the Compound Having Formula (L2a)

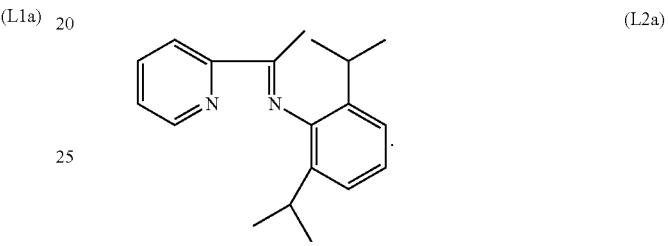

(L2a)

In a 500 ml flask, to a solution of 2,6-di-iso-propylaniline (13.3 g, 75 mmol) in methanol (300 ml), was added 2-acetylpyridine (9.1 g, 75 mmol): the mixture obtained was left, under stirring, at room temperature, for 48 hours. The precipitate obtained was filtered and subsequently dried under vacuum, to obtain 14 g of a yellow crystalline powder (yield=67%) corresponding to the compound having formula (L2a).

Elemental analysis [found (calculated)]: C: 81.37% (81.38%); H: 8.64% (8.63%); N: 10.01% (9.99%).

$^1$H-NMR (CDCl$_3$, δ ppm) 8.69 (d, 1H, PyH), 8.38 (d, 1H, PyH), 7.82 (t, 1H, PyH), 7.39 (m, 1H, PyH), 7.11-7.20 (m, 3H, ArH), 2.75 (m, 2H, CHMe$_2$), 2.21 (s, 3H, N=CH-Me), 1.15 (d, 12H, CH(CH$_3$)$_2$).

2.2 Synthesis of the Ligand Having Formula (L2)

Into a 2 liter reactor, provided with a stirrer, were loaded 24 g (85 mmol) of the compound having formula (L2a) obtained as described above and 900 ml of anhydrous methanol: the whole was cooled to 0° C. and subsequently sodium boron hydride (48.6 g, 1285 mmol) was added in small portions. The mixture obtained was left, under stirring, at room temperature, overnight, and subsequently quenched with brine and extracted using ethyl acetate. The solvent was subsequently removed by distillation at reduced pressure, and the residue obtained was purified by elution in a silica gel chromatography column [eluent: hexane/ethyl acetate mixture in 9/1 ratio (v/v)], and subsequently treated with cold ethyl ether, to obtain 11 g of a white crystalline solid (yield=46%) corresponding to the ligand having formula (L2).

Elemental analysis [found (calculated)]: C: 81.03% (80.80%); H: 9.42% (9.28%); N: 10.01% (9.92%).

GC-MS: M$^+$=m/z 282; [M-C$_3$H$_7$]$^+$=m/z 239; [M-C$_7$H$_8$N]$^+$=m/z 176; [M-C$_{12}$H$_{18}$N]$^+$=m/z 106.

$^1$H-NMR (CDCl$_3$, δ ppm): 8.64 (d, 1H, HPy), 7.53 (dt, 1H, HPy), 7.2 (d, 1H, HPy), 7.00-7.12 (m, 1H, HPy; m, 3H, ArH), 4.0-4.2 (m, 1H, NCH(CH₃); m, 1H, NH), 3.30 (sept, 2H, —CH(CH₃)₂), 1.55 (d, 3H, —NCH(CH₃)), 1.10 (s, 12H, —CH(CH₃)₂).

Example 3

Synthesis of the Ligand Having Formula (L3)

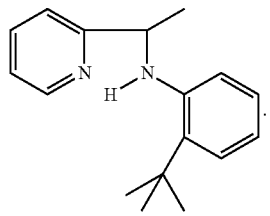

(L3)

3.1 Synthesis of the Compound Having Formula (L3a)

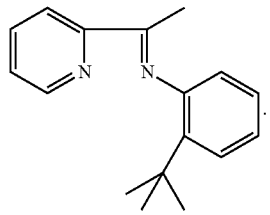

(L3a)

In a 500 ml flask, to a solution of 2-tert-butylaniline (15.89 g, 106.5 mmol) in methanol (300 ml), was added 2-acetylpyridine (12.9 g, 106.5 mmol): the mixture obtained was left, under stirring, at room temperature, for 48 hours. The solvent was subsequently removed by evaporation and the residue obtained was crystallized using methanol, to obtain 20 g of a yellow crystalline powder (yield=75%) corresponding to the compound having formula (L3a).

Elemental analysis [found (calculated)]: C: 81.17% (80.91%); H: 8.14% (7.99%); N: 10.91% (11.10%).

3.2 Synthesis of the Ligand Having Formula (L3)

Into a 2 liter reactor, provided with a stirrer, were loaded 28 g (111 mmol) of the compound having formula (L3a) obtained as described above and 800 ml of anhydrous methanol: the whole was cooled to 0° C. and subsequently sodium boron hydride (38 g, 1004 mmol) was added in small portions. The mixture obtained was left, under stirring, at room temperature, overnight, and subsequently quenched with brine and extracted using ethyl acetate. The solvent was subsequently removed by distillation at reduced pressure, and the residue obtained was purified by elution in a silica gel chromatography column [eluent: hexane/ethyl acetate mixture in 9/1 ratio (v/v)], and subsequently treated with cold ethyl ether, to obtain 11 g of a white crystalline solid (yield=39%) corresponding to the ligand having formula (L3).

Elemental analysis [found (calculated)]: C: 80.00% (80.27%); H: 9.12% (8.72%); N: 11.31% (11.01%).

GC-MS: $M^+$=m/z 254; $[M-CH_3]^+$=m/z 239; $[M-C_4H_9]^+$=m/z 197; m/z=183; m/z 132 $C_7H_{10}N_2$; $[M-C_{10}H_{14}N]^+$=m/z 106; $[M-C_{12}H_{18}N]^+$=m/z 78.

¹H-NMR (CDCl₃, δ ppm): 8.64 (d, 1H, HPy), 7.7 (td, 1H, PyH), 7.36 (d, 1H, HPy), 7.25 (d, 1H, ArH), 7.18 (td, 1H, PyH), 6.98 (td, 1H, PyH), 6.98 (td, 1H, PyH), 6.48 (d, 1H, PyH), 5.0 (broad s, 1H, NH), 4.7 (q, 1H, NCH(CH₃)), 1.57 (d, 3H, —NCH(CH₃)), 1.5 (s, 9H, —C(CH₃)₃).

Example 4

Synthesis of the Ligand Having Formula (L4)

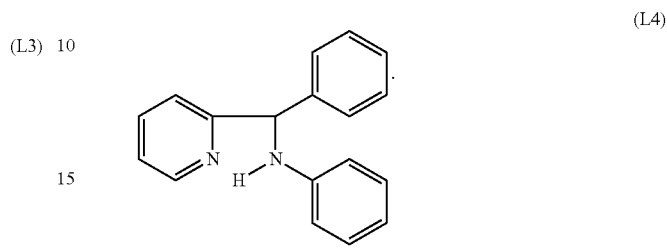

(L4)

4.1 Synthesis of the Compound Having Formula (L4a)

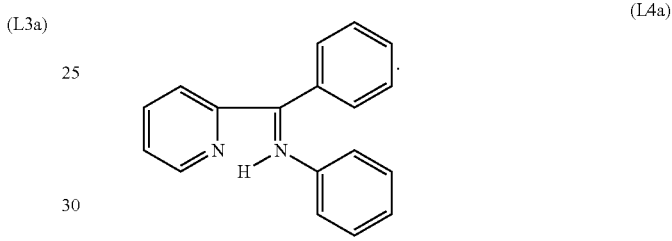

(L4a)

In a 500 ml flask, to a solution of 2-benzoylpyridine (20 g, 109 mmol) in methanol (200 ml), were added aniline (11.2 g, 120 mmol) and a few drops of formic acid: the mixture obtained was left, under stirring, at room temperature, for 48 hours. Subsequently, the mixture obtained was dried under vacuum and the residue obtained was purified by elution in a silica gel chromatography column [eluent: heptane/ethyl acetate mixture in 99/1 ratio (v/v)], to obtain 14.4 g of a yellowish oil (yield=51%) corresponding to the compound having formula (L4a).

Elemental analysis [found (calculated)]: C: 84.00% (83.69%); H: 5.83% (5.46%); N: 11.52% (10.84%).

GC-MS: $M^+$=m/z 258; m/z 180, 155, 77, 51.

4.2 Synthesis of the Ligand Having Formula (L4)

Into a 2 liter reactor, provided with a stirrer, were loaded 14 g (85 mmol) of the compound having formula (L4a) obtained as described above and 900 ml of anhydrous methanol: the whole was cooled to 0° C. and subsequently sodium boron hydride (31 g, 819 mmol) was added in small portions. The mixture obtained was left, under stirring, at room temperature, overnight, and subsequently quenched with brine and extracted using ethyl acetate. The solvent was subsequently removed by distillation at reduced pressure, and the residue obtained was purified by elution in a silica gel chromatography column [eluent: hexane/ethyl acetate mixture in 9/1 ratio (v/v)], and subsequently treated with cold ethyl ether, to obtain 12.5 g of a white crystalline solid (yield=56.5%) corresponding to the ligand having formula (L4).

Elemental analysis [found (calculated)]: C: 83.30% (83.04%); H: 6.87% (6.19%); N: 11.01% (10.76%).

GC-MS: $M^+$=m/z 260; m/z 182, 168, 104, 77 51.

¹H-NMR (CDCl₃, δ ppm): 8.6 (m 1H, PyH), 7.62-7.69 (m 1H, PyH), 7.45-7.50 (m 2H, ArH), 7.30-7.38 (m, 1H, HPy;

m 2H, ArH), 7.23-7.27 (m, 1H, ArH), 7.18-7.21 (m, 1H, PyH), 7.05-7.13 (m, 2H, NH—ArH), 6.60-6.65 (m, 3H, NH—ArH), 5.55 (s, 1H, NH), 5.50 (s, 1H, —NCH).

Example 5

Synthesis of the Ligand Having Formula (L5)

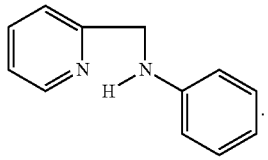

(L5)

5.1 Synthesis of the Compound Having Formula (L5a)

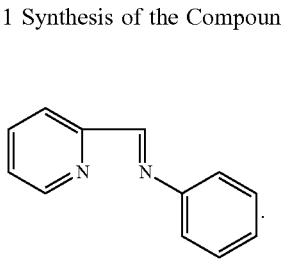

(L5a)

In a 500 ml flask, to a solution of aniline (26.1 g, 280 mmol) in methanol (250 ml), were added 2-pyridinecarboxyaldehyde (30 g, 280 mmol) and a few drops of formic acid: the mixture obtained was left, under stirring, at room temperature, for 48 hours. Subsequently, the mixture obtained was dried under vacuum and the residue obtained was purified by elution in a silica gel chromatography column [eluent: heptane/ethyl acetate mixture in 99/1 ratio (v/v)], to obtain 38 g of a yellowish solid (yield=74.5%) corresponding to the compound having formula (L5a).

Elemental analysis [found (calculated)]: C: 80.00% (79.10%); H: 5.83% (5.53%); N: 15.71% (15.37%).

$^1$H-NMR (CDCl$_3$, δ ppm) 8.70 (d, 1H, HPy), 8.59 (s, 1H CH=N), 8.19 (d, 1H, HPy), 7.77 (dt, 1H, HPy), 7.23-7.42 (m, 1H, HPy; m, 5H, Ar).

5.2 Synthesis of the Ligand Having Formula (L5)

Into a 2 liter reactor, provided with a stirrer, were loaded 13 g (71.3 mmol) of the compound having formula (L5a) obtained as described above and 700 ml of anhydrous methanol: the whole was cooled to 0° C. and subsequently sodium boron hydride (40 g, 1057 mmol) was added in small portions. The mixture obtained was left, under stirring, at room temperature, overnight, and subsequently quenched with brine and extracted using ethyl acetate. The solvent was subsequently removed by distillation at reduced pressure, and the residue obtained was purified by elution in a silica gel chromatography column [eluent: hexane/ethyl acetate mixture in 9/1 ratio (v/v)], and subsequently treated with cold ethyl ether, to obtain 9.12 g of a white crystalline solid (yield=69.5%) corresponding to the ligand having formula (L5).

GC-MS: M$^+$=m/z 184; [M-C$_6$H$_6$N]$^+$=m/z 106; [M-C$_7$H$_7$N$_2$]$^+$=m/z 77.

$^1$H-NMR (CDCl$_3$, δ ppm): 8.60 (dd, 1H, PyH), 7.64 (m, 1H, PyH), 7.35 (d, 1H, PyH), 7.22-7.17 (m, 1H, Py, 2H, ArH), 6.75 (dt, 1H, ArH), 6.69 (d, 2H, ArH), 4.8 (s, 1H, NH), 4.48 (s, 2H, Py-CH$_2$N).

Example 6

Synthesis of the Ligand Having Formula (L6)

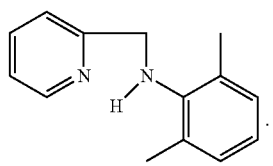

(L6)

6.1 Synthesis of the Compound Having Formula (L6a)

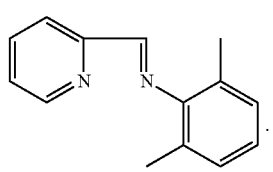

(L6a)

In a 500 ml flask, to a solution of 2,6-dimethylaniline (31 g, 250 mmol) in methanol (250 ml), were added 2-pyridinecarboxyaldehyde (26.8 g, 250 mmol) and a few drops of formic acid: the mixture obtained was left, under stirring, at room temperature, for 24 hours. Subsequently, the mixture obtained was dried over sodium sulphate and filtered, and the solvent was removed by evaporation under vacuum: the residue obtained was washed with cold methanol, to obtain 47 g of an orange solid (yield=89%) corresponding to the compound having formula (L6a).

Elemental analysis [found (calculated)]: C: 80.00% (79.97%); H: 6.81% (6.71%); N: 13.71% (13.37%).

$^1$H-NMR (CDCl$_3$, δ ppm) 8.70 (d, 1H, HPy), 8.33 (s, 1H, CH=N), 8.23 (d, 1H, HPy), 7.82 (dt, 1H, HPy), 7.38 (ddd, 1H, HPy), 6.91-7.15 (m, 5H, Ar), 2.16 (s, 6H, Ar—CH$_3$).

6.2 Synthesis of the Ligand Having Formula (L6)

Into a 2 liter reactor, provided with a stirrer, were loaded 18 g (85.6 mmol) of the compound having formula (L6a) obtained as described above and 800 ml of anhydrous methanol: the whole was cooled to 0° C. and subsequently sodium boron hydride (24 g, 634 mmol) was added in small portions. The mixture obtained was left, under stirring, at room temperature, overnight, and subsequently quenched with brine and extracted using ethyl acetate. The solvent was subsequently removed by distillation at reduced pressure, and the residue obtained was purified by elution in a silica gel chromatography column [eluent: hexane/ethyl acetate mixture in 9/1 ratio (v/v)], and subsequently treated with cold ethyl ether, to obtain 9.15 g of a white crystalline solid (yield=50.4%) corresponding to the ligand having formula (L6).

GC-MS: M$^+$=m/z 212; [M-C$_6$H$_6$N]$^+$=m/z 120.

$^1$H-NMR (CDCl$_3$, δ ppm): 8.63 (d, 1H, PyH), 7.65 (dt, 1H, PyH), 7.27 (d, 1H, PyH), 7.20 (dd, 1H, PyH), 7.02 (d, 2H, ArH), 6.85 (m, 1H, ArH), 4.4 (broad s, 1H, NH), 4.31 (s, 2H, Py-CH$_2$N), 2.35 (s, 6H, ArCH$_3$).

Example 7

Synthesis of the Ligand Having Formula (L7)

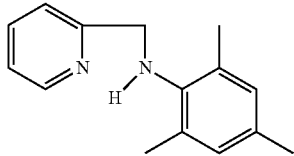
(L7)

7.1 Synthesis of the Compound Having Formula (L7a)

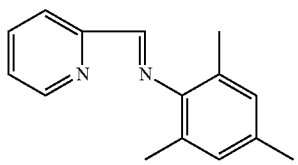
(L7a)

In a 500 ml flask, to a solution of 2,4,6-trimethylaniline (12.6 g, 93 mmol) in methanol (250 ml), were added 2-pyridinecarboxyaldehyde (10 g, 93 mmol) and a few drops of formic acid: the mixture obtained was left, under stirring, at room temperature, for 48 hours. Subsequently, the solvent was removed by evaporation under vacuum and the oily residue obtained was purified by elution in a silica gel chromatoghraphy column [eluent: heptane/ethyl acetate mixture in 99/1 ratio (v/v)], to obtain 17 g of a yellowish solid (yield=81%) corresponding to the compound having formula (L7a).

Elemental analysis [found (calculated)]: C: 80.56% (80.32%); H: 7.22% (7.19%); N: 13.11% (12.49%).

GC-MS: $M^+$=m/z 224; $[M-CH_3]^+$=m/z 209; $[M-C_5H_4N]^+$=m/z 146.

$^1$H-NMR (CDCl$_3$, δ ppm) 8.70 (m, 1H, HPy), 8.35 (s, 1H CH=N), 8.29 (d, 1H, HPy), 7.84 (tdd, 1H, HPy), 7.41 (m, 1H, HPy), 6.91 (s, 2H ArH), 2.31 (s, 3H Ar(CH$_3$)), 2.10 (s, 6H Ar(CH$_3$)$_2$).

7.2 Synthesis of the Ligand Having Formula (L7)

Into a 2 liter reactor, provided with a stirrer, were loaded 13 g (58 mmol) of the compound having formula (L7a) obtained as described above, 80 ml of anhydrous methanol, 80 ml of chloroform, and sodium boron hydride (2.2 g, 58 mmol) in small portions. The mixture obtained was left, under stirring, at room temperature, overnight. The solvents were subsequently removed by distillation at reduced pressure, and the residue obtained was extracted using a mixture of ethyl acetate (50 ml) and water (50 ml). The organic extracts obtained were washed using water until neutral, anhydrified over sodium sulphate, filtered, and subjected to distillation at reduced pressure to remove the remaining solvent, to obtained an oily yellow-coloured residue. To said oily residue were added 25 ml of cold heptane, to obtain 5.15 g of a white crystalline solid (yield=39%) corresponding to the ligand having formula (L7).

GC-MS: $M^+$=m/z 226; $[M-C_6H_6N]^+$=m/z 134.

$^1$H-NMR (CDCl$_3$, δ ppm): 8.59 (d, 1H, PyH), 7.65 (dt, 1H, PyH), 7.27 (d, 1H, PyH), 7.20 (m, 1H, PyH), 6.8 (d, 2H, ArH), 4.2 (s, 2H, Py-CH$_2$N), 4.1 (broad s, 1H, NH), 2.28 (s, 6H, ArCH$_3$), 2.2 (s, 3H, Ar—CH$_3$).

Example 8

Synthesis of ZrCl$_3$(L1) [Sample BM2-199]

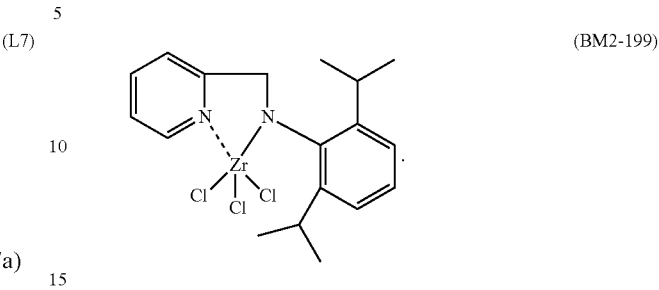
(BM2-199)

Zirconium tetrachloride (ZrCl$_4$) (0.500 g; 2.14 mmol) was introduced into a 100 ml long-necked flask together with a solution of the ligand having formula (L1) (0.599 g; 2.22 mmol; L1/Zr molar ratio=1.03), obtained as described in Example 1, in toluene (15 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.66 g (yield=66%) of a clear yellow microcrystalline solid product corresponding to the ZrCl$_3$(L1) complex.

Elemental analysis [found (calculated)]: C: 45.87% (46.49%); H: 4.65% (4.98%); N: 5.45% (6.02%); Zr: 18.72% (19.62%); Cl: 21.65% (22.87%).

FIG. 1 shows the FTIR-ATR spectrum of the ZrCl$_3$(L1) complex obtained.

Figure 2:
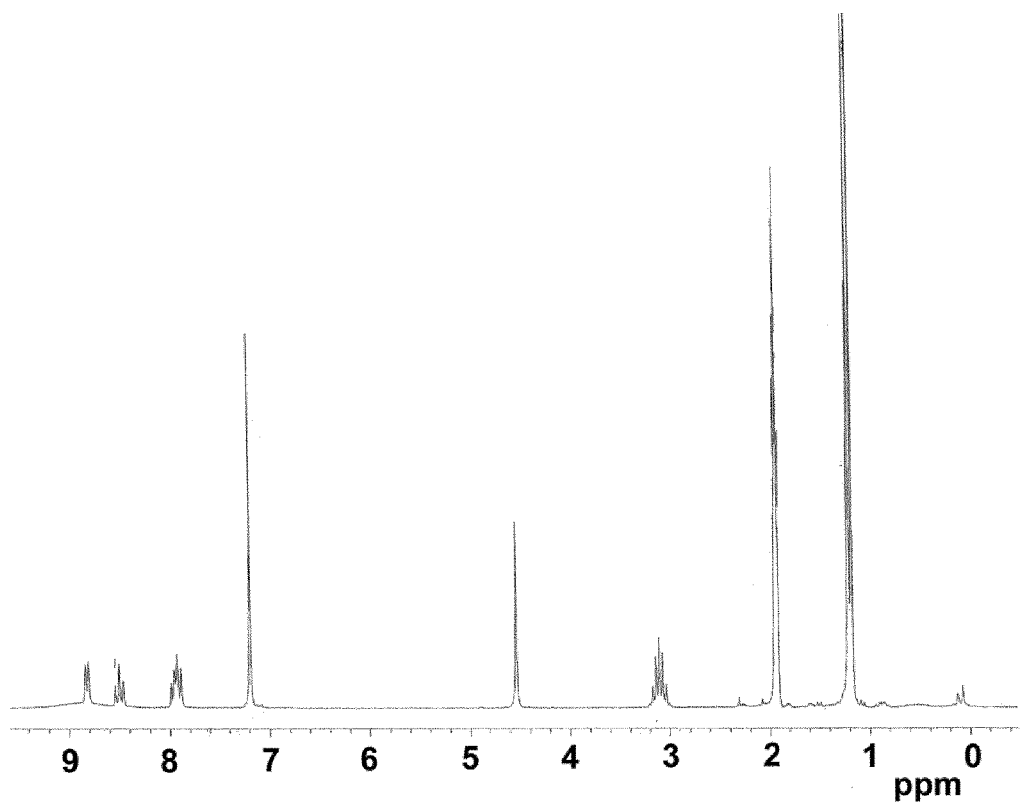
FIG. 2. Illustrated is a $^1$H-NMR spectrum of the $ZrCl_3$ (L1) complex obtained from the synthesis described in Example 8.

FIG. 2 shows the $^1$H-NMR spectrum of the ZrCl$_3$(L1) complex obtained.

Example 9

Synthesis of ZrCl$_3$(L2) [Sample BM2-207]

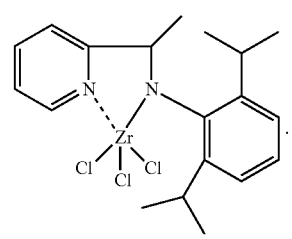
(BM2-207)

Zirconium tetrachloride (ZrCl$_4$) (0.398 g; 1.71 mmol) was introduced into a 100 ml long-necked flask together with a solution of the ligand having formula (L2) (0.507 g; 1.80 mmol; L2/Zr molar ratio=1.05), obtained as described in Example 2, in toluene (10 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.71 g (yield=86%) of a clear yellow microcrystalline solid product corresponding to the ZrCl$_3$(L2) complex.

Elemental analysis [found (calculated)]: C: 46.87% (47.64%); H: 4.85% (5.26%); N: 5.21% (5.84%); Zr: 19.87% (19.04%); Cl: 21.89% (22.20%).

Figure 3:
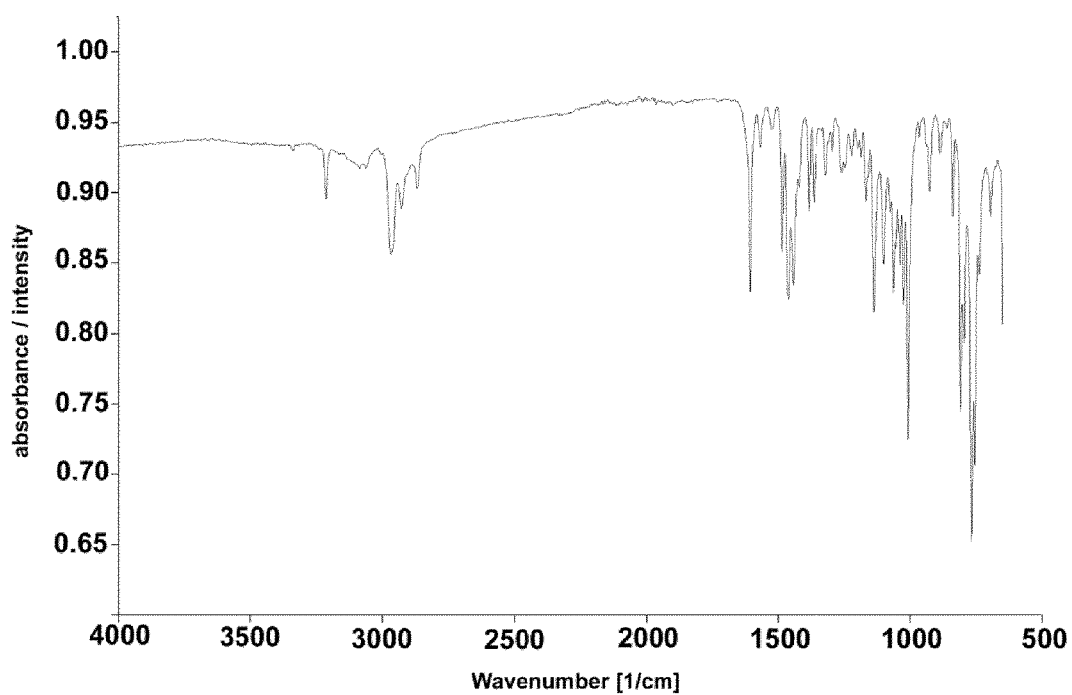
FIG. 3. Illustrated is a FTIR-ATR spectrum of the $ZrCl_3$ (L2) complex obtained from the synthesis described in Example 9.

FIG. 3 shows the FTIR-ATR spectrum of the ZrCl₃(L2) complex obtained.

Figure 4:
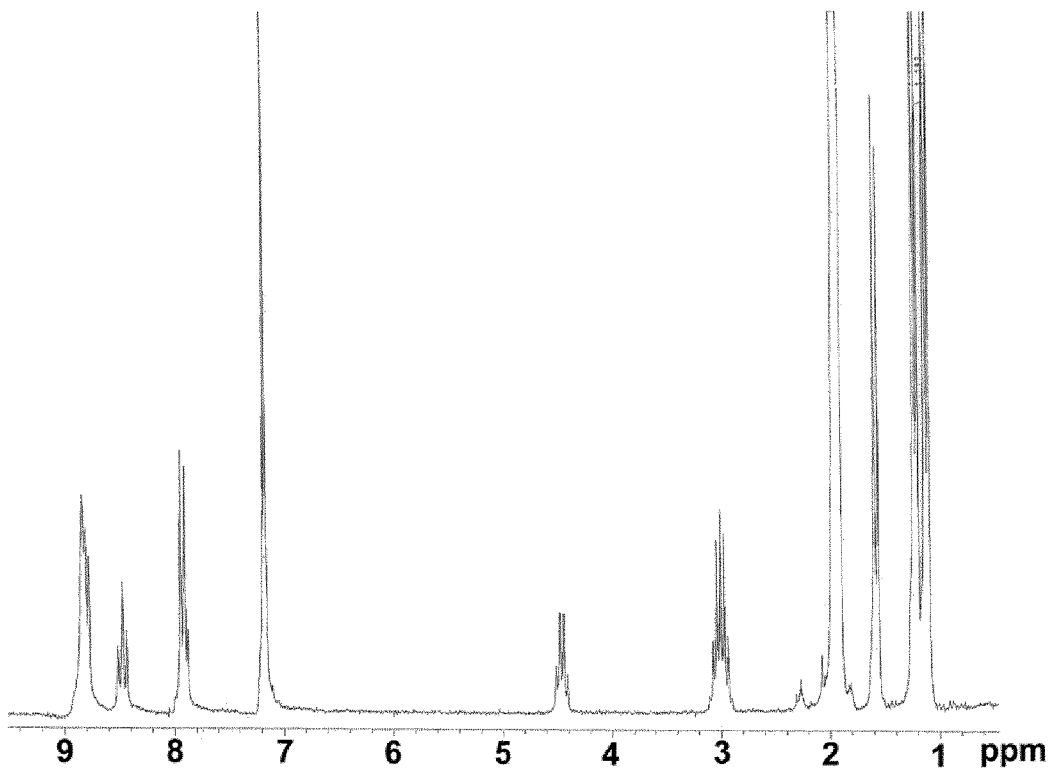
FIG. 4. Illustrated is a $^1$H-NMR spectrum of the $ZrCl_3$ (L2) complex obtained from the synthesis described in Example 9.

FIG. 4 shows the ¹H-NMR spectrum of the ZrCl₃(L2) complex obtained.

Example 10

Synthesis of ZrCl₃(L3) [Sample MT-2]

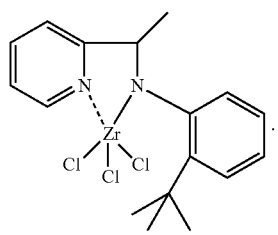

(MT-2)

Zirconium tetrachloride (ZrCl₄) (0.525 g; 2.25 mmol) was introduced into a 100 ml long-necked flask together with a solution of the ligand having formula (L3) (0.570 g; 2.24 mmol; L3/Zr molar ratio=1), obtained as described in Example 3, in toluene (10 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.81 g (yield=80%) of a clear yellow microcrystalline solid product corresponding to the ZrCl₃(L3) complex.

Elemental analysis [found (calculated)]: C: 44.82% (45.28%); H: 4.05% (4.69%); N: 5.95% (6.21%); Zr: 19.99% (20.23%); Cl: 23.00% (23.58%).

Example 11

Synthesis of ZrCl₃(L5) [Sample MT-4]

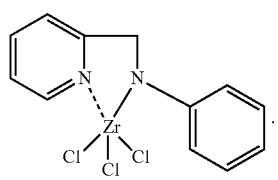

(MT-4)

Zirconium tetrachloride (ZrCl₄) (0.368 g; 1.58 mmol) was introduced into a 100 ml long-necked flask together with a solution of the ligand having formula (L5) (0.289 g; 1.58 mmol; L5/Zr molar ratio=1), obtained as described in Example 5, in toluene (10 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.26 g (yield=43%) of a clear yellow microcrystalline solid product corresponding to the ZrCl₃(L5) complex.

Elemental analysis [found (calculated)]: C: 36.87% (37.85%); H: 2.65% (2.91%); N: 6.95% (7.36%); Zr: 22.98% (23.95%); Cl: 27.42% (27.93%).

Figure 5:
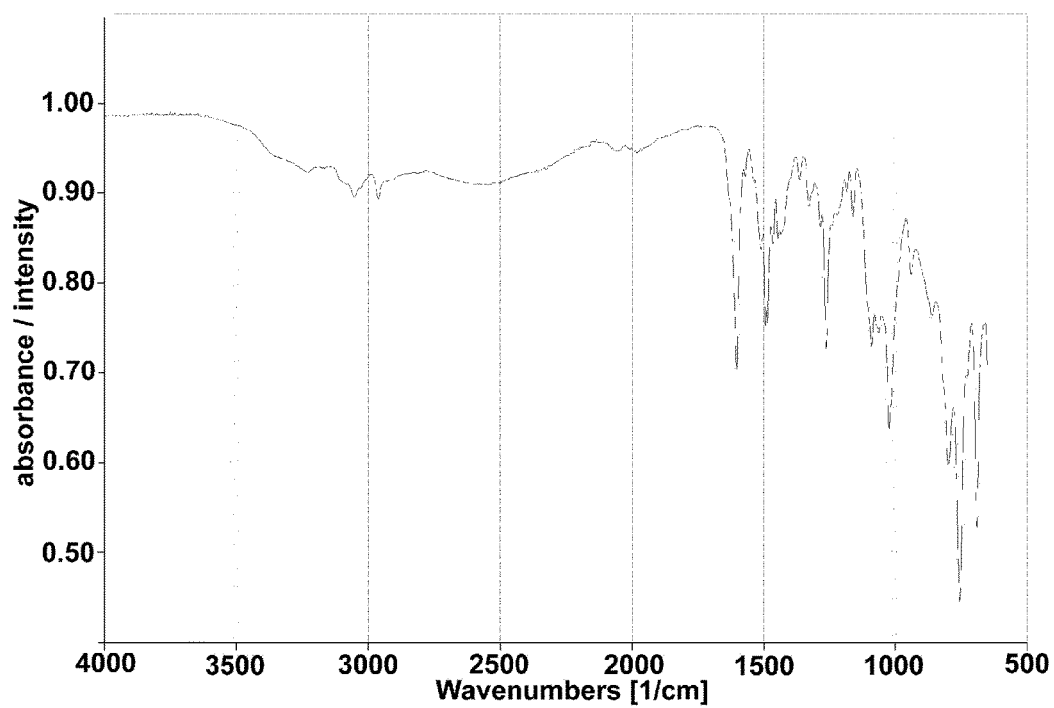
FIG. 5. Illustrated is a FTIR-ATR spectrum of the $ZrCl_3$ (L5) complex obtained from the synthesis described in Example 11.

FIG. 5 shows the FTIR-ATR spectrum of the ZrCl₃(L5) complex obtained.

Example 12

Synthesis of ZrCl₃(L6) [Sample MT-30]

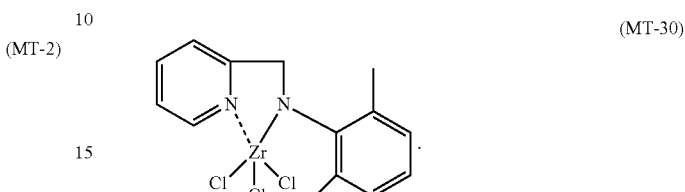

(MT-30)

Zirconium tetrachloride (ZrCl₄) (0.317 g; 1.36 mmol) was introduced into a 100 ml long-necked flask together with a solution of the ligand having formula (L6) (0.289 g; 1.36 mmol; L6/Zr molar ratio=1), obtained as described in Example 6, in toluene (10 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.50 g (yield=90%) of a clear yellow microcrystalline solid product corresponding to the ZrCl₃(L6) complex.

Elemental analysis [found (calculated)]: C: 41.52% (41.12%); H: 3.15% (3.70%); N: 6.15% (6.85%); Zr: 21.95% (22.31%); Cl: 25.75% (26.01%).

Example 13

Synthesis of ZrCl₃(L7) [Sample MT-52]

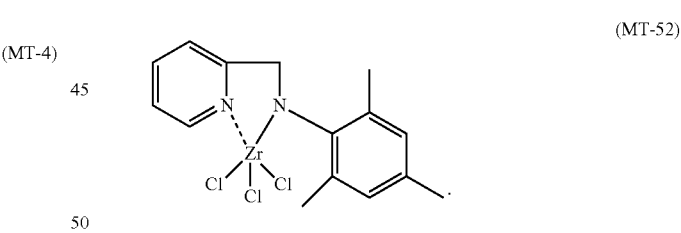

(MT-52)

Zirconium tetrachloride (ZrCl₄) (0.351 g; 1.51 mmol) was introduced into a 100 ml long-necked flask together with a solution of the ligand having formula (L7) (0.341 g; 1.51 mmol; L7/Zr molar ratio=1), obtained as described in Example 7, in toluene (10 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.50 g (yield=78%) of a clear yellow microcrystalline solid product corresponding to the ZrCl₃(L7) complex.

Elemental analysis [found (calculated)]: C: 42.00% (42.60%); H: 3.75% (4.05%); N: 6.01% (6.62%); Zr: 20.87% (21.57%); Cl: 24.98% (25.15%).

Example 14

Synthesis of ZrCl$_3$(L4) [Sample MT-56]

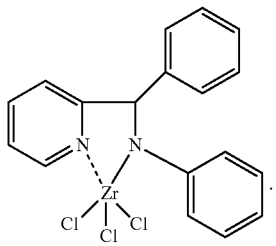

(MT-56)

Zirconium tetrachloride (ZrCl$_4$) (0.212 g; 0.910 mmol) was introduced into a 100 ml long-necked flask together with a solution of the ligand having formula (L4) (0.236 g; 0.910 mmol; L4/Zr molar ratio=1), obtained as described in Example 4, in toluene (10 ml). The mixture obtained was left, under stirring, at room temperature, for 30 minutes, and subsequently heated under reflux for 2 hours. The solid formed was recovered by filtration, washed with heptane (2×2 ml) and dried at reduced pressure, at room temperature, to obtain 0.245 g (yield=62%) of a clear yellow microcrystalline solid product corresponding to the ZrCl$_3$(L4) complex.

Elemental analysis [found (calculated)]: C: 46.88% (47.32%); H: 3.01% (3.30%); N: 5.76% (6.13%); Zr: 29.44% (19.96%); Cl: 24.01% (23.27%).

Example 15

Synthesis of ZrCl$_2$(L5)$_2$ [Sample MT-81]

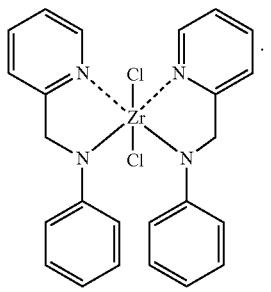

(MT-81)

Into a 100 ml long-necked flask was introduced a solution of the ligand having formula (L5) (0.38 g; 2.08 mmol), obtained as described in Example 5, in tetrahydrofuran (10 ml): the whole was cooled to −70° C. and subsequently a solution of lithium-n-butyl (0.87 ml, 2.17 mmol) in hexane was added drop by drop, to obtain a yellow-orange suspension. The suspension obtained was heated to room temperature and left, under stirring, at this temperature, for 3 hours. Subsequently, a solution of zirconium tetrachloride tetrahydrofuran (1:2) [ZrCl$_4$(THF)$_2$] (0.391 g; 1.04 mmol; L5/Zr molar ratio=2) in tetrahydrofuran (30 ml) was added drop by drop: after the addition of the first 10 ml an orange solution was obtained, whilst at the end of the addition a yellow solution was obtained, which was left, under stirring, at room temperature, for one night. Subsequently, the solvent was removed by distillation at reduced pressure, at room temperature, to obtain a yellow residue, which was treated with dichloromethane (15 ml). The suspension obtained was filtered and the filtrate was concentrated to half volume, treating with hexane (20 ml), and kept at −30° C. for one night. Subsequently, the residue obtained was recovered by filtration, washed with heptane (2×1 ml) and dried under vacuum, at room temperature, to obtain 0.27 g (yield=35%) of a brown microcrystalline solid product corresponding to the ZrCl$_2$(L5)$_2$ complex.

Elemental analysis [found (calculated)]: C. 53.79% (53.54%); H: 3.89% (4.19%); N: 10.99% (10.60%); Zr: 18.01% (17.26%); Cl: 12.98% (13.41%).

Example 16 (GL957)

Into a 50 ml test tube were condensed, in the cold (−20° C.), 2 ml of 1,3-butadiene, equal to approximately 1.4 g. Subsequently, 4.65 ml of toluene were added and the temperature of the solution thus obtained was brought to 20° C. Subsequently, methylaluminoxane (MAO) in a toluene solution (15.75 ml; 2.5×10$^{-2}$ mol, equal to approximately 1.45 g) was added, followed by the ZrCl$_3$(L1) complex [sample BM2-199] (4.6 ml of toluene solution at a concentration of 5 mg/ml; 5×10$^{-5}$ mol, equal to approximately 23 mg) obtained as described in Example 8. The whole was kept, under magnetic stirring, at 20° C., for 6 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 0.97 g of polybutadiene having a content of 1,4-trans units of 96%: further features of the process and of the polybutadiene obtained are shown in Table 1.

FIG. 6(a) shows the FT-IR spectrum of the polybutadiene obtained.

Example 17 (GL959)

Into a 50 ml test tube were condensed, in the cold (−20° C.), 2 ml of 1,3-butadiene, equal to approximately 1.4 g. Subsequently, 4.45 ml of toluene were added and the temperature of the solution thus obtained was brought to 20° C. Subsequently, methylaluminoxane (MAO) in a toluene solution (15.75 ml; 2.5×10$^{-2}$ mol, equal to approximately 1.45 g) was added, followed by the ZrCl$_3$(L2) complex [sample BM2-207] (4.8 ml of toluene solution at a concentration of 5 mg/ml; 5×10$^{-5}$ mol, equal to approximately 24 mg) obtained as described in Example 9. The whole was kept, under magnetic stirring, at 20° C., for 7 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 0.63 g of polybutadiene having a content of 1,4-trans units of 95%: further features of the process and of the polybutadiene obtained are shown in Table 1.

FIG. 6(b) shows the FT-IR spectrum of the polybutadiene obtained.

Figure 7:
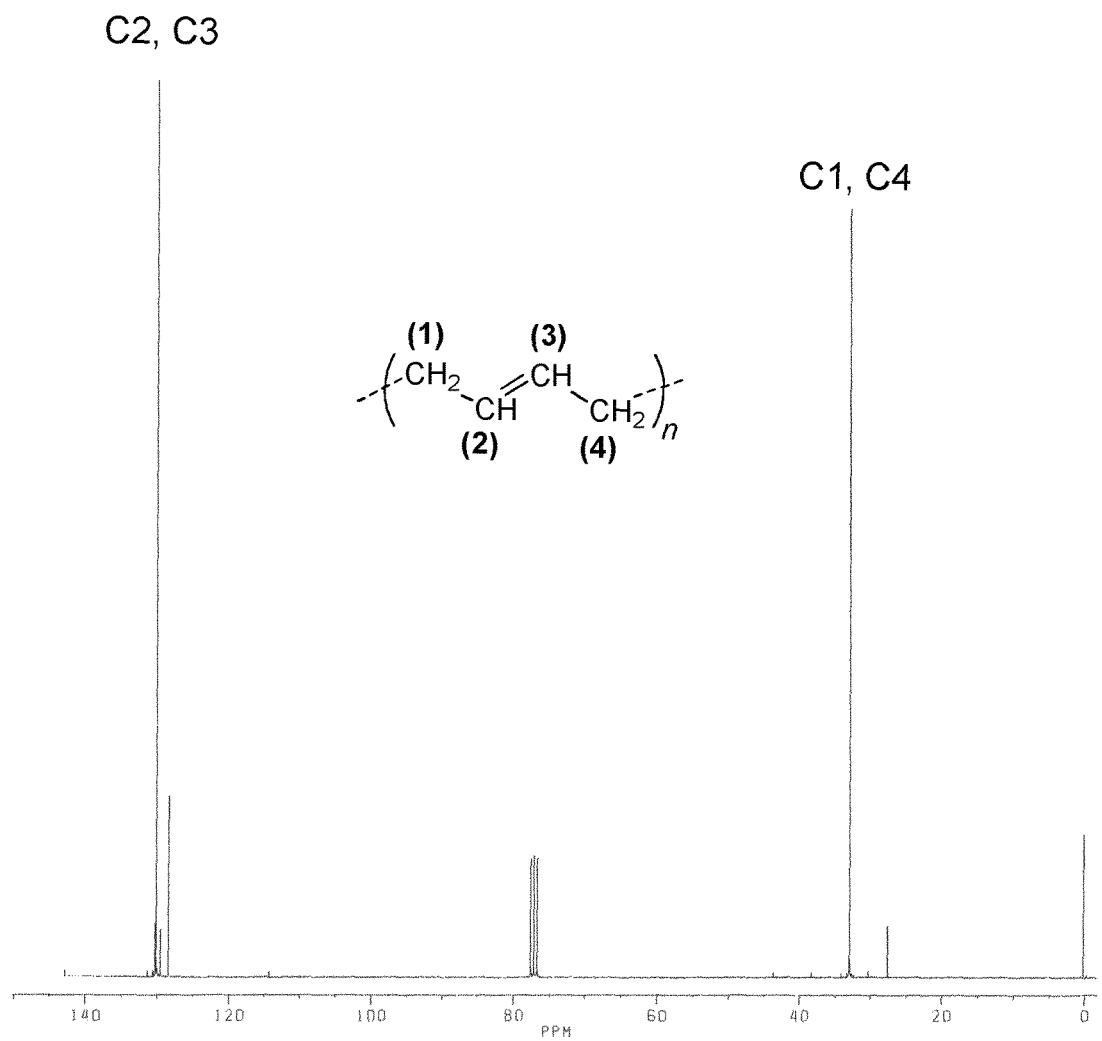
FIG. 7. Illustrated is a $^{13}$C-NMR spectrum of the polybutadiene obtained in Example 17.

FIG. 7 shows the $^{13}$C-NMR spectrum of the polybutadiene obtained.

Figure 12:
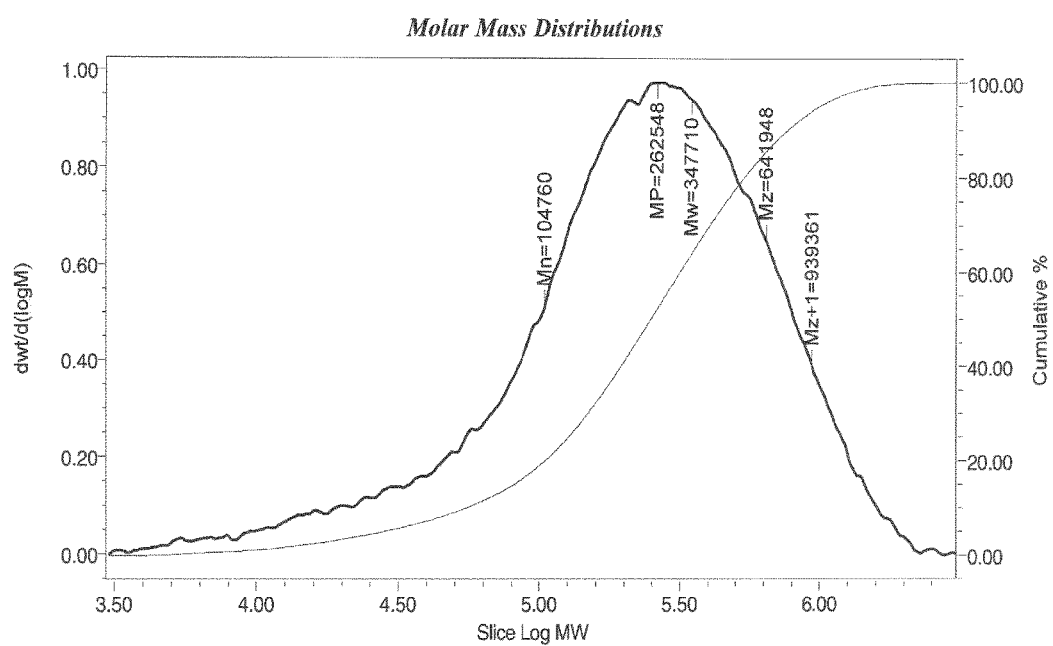
FIG. 12. Illustrated is a GPC diagram of the polybutadiene obtained in Example 17.

FIG. 12 shows the GPC diagram of the polybutadiene obtained.

Example 18 (MM20)

Into a first 50 ml test tube were condensed, in the cold (−20° C.), 2 ml of 1,3-butadiene, equal to approximately 1.4 g. Subsequently, 10.1 ml of toluene were added and the temperature of the solution thus obtained was brought to 20° C. Subsequently, dry methylaluminoxane (MAOdry) in a toluene solution (10 ml; $3\times10^{-2}$ mol, equal to approximately 1.74 g) was added. Into a second 10 ml test tube were introduced the $ZrCl_3(L2)$ complex [sample BM2-207] (2.9 ml of toluene solution at a concentration of 5 mg/ml; $3\times10^{-5}$ mol, equal to approximately 14.4 mg) obtained as described in Example 9 and tri-ethyl-aluminium (2 ml of toluene solution at a concentration of 0.052 g/ml; $9\times10^4$ mol, equal to approximately 104 mg): the whole was kept, under stirring, at room temperature, for 10 minutes, and the solution obtained was completely added to said first test tube. The whole was kept, under magnetic stirring, at 20° C., for 2 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 1.24 g of polybutadiene having a content of 1,4-trans units of 99%: further features of the process and of the polybutadiene obtained are shown in Table 1.

Figure 6:
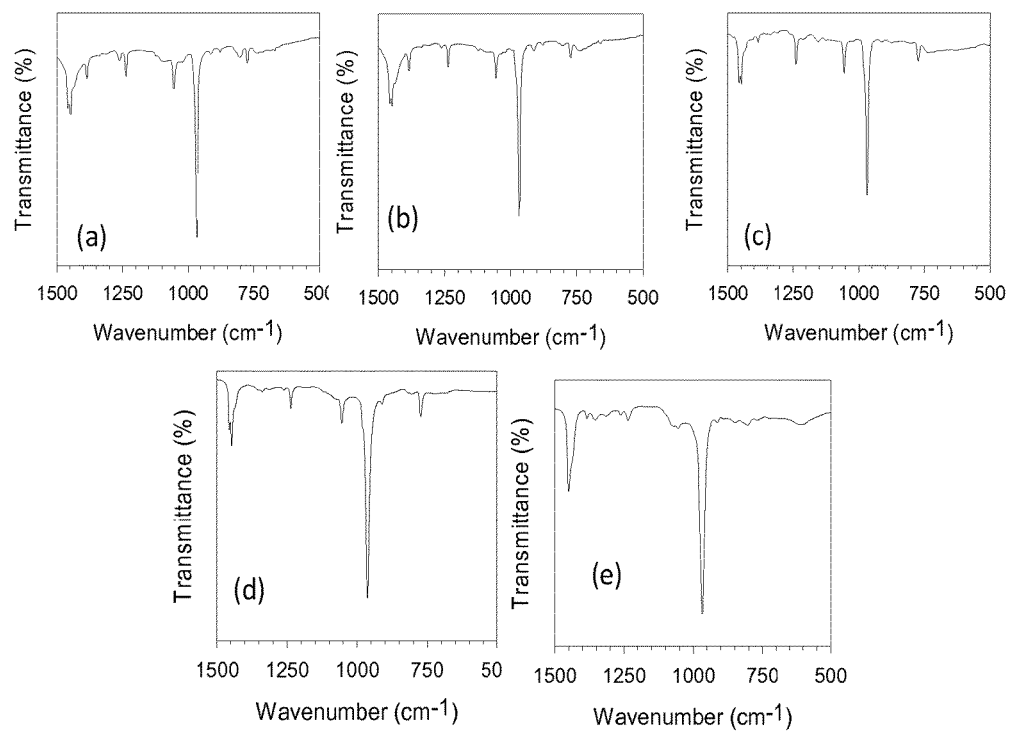
FIG. 6. Illustrated are FT-IR spectra of polybutadienes listed in Table 1. The spectrum in (a) was obtained from the synthesis described in Example 16; spectrum (b) from Example 17; spectrum (c) from Example 18; spectrum (d) from Example 19; and spectrum (e) from Example 21.

FIG. 6(*c*) shows the FT-IR spectrum of the polybutadiene obtained.

Figure 8:
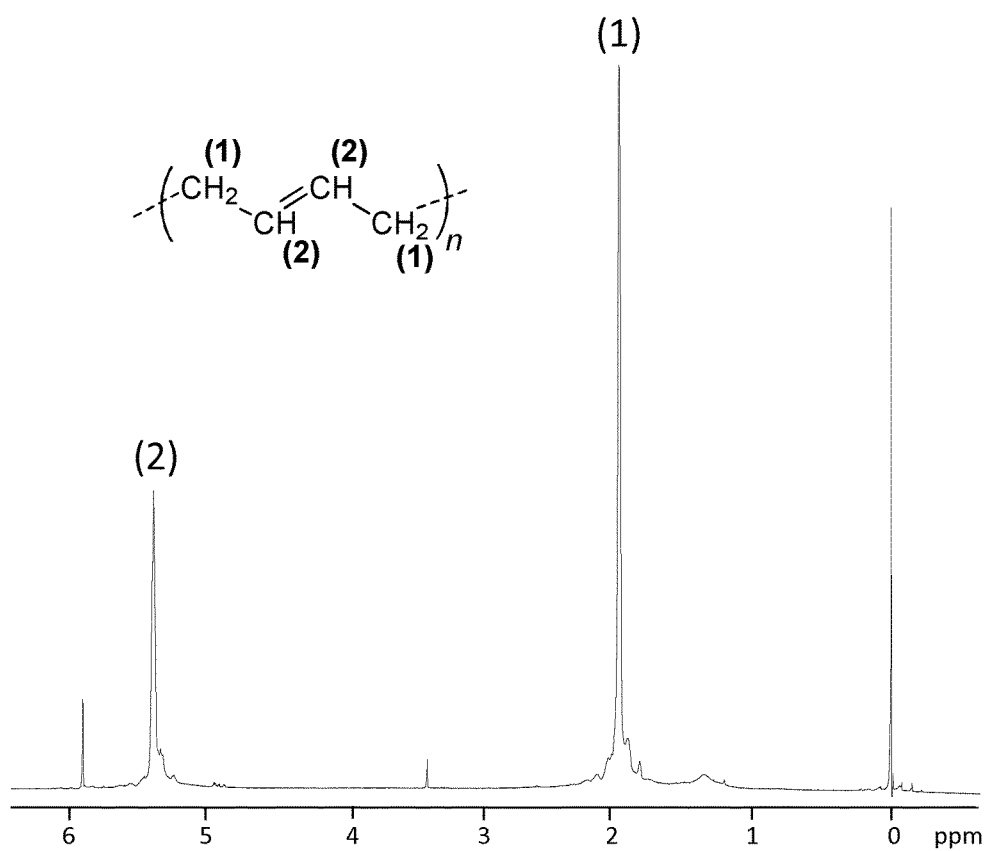
FIG. 8. Illustrated is a $^1$H-NMR spectrum of the polybutadiene obtained in Example 18.

FIG. 8 shows the $^1$H-NMR spectrum of the polybutadiene obtained.

Figure 9:
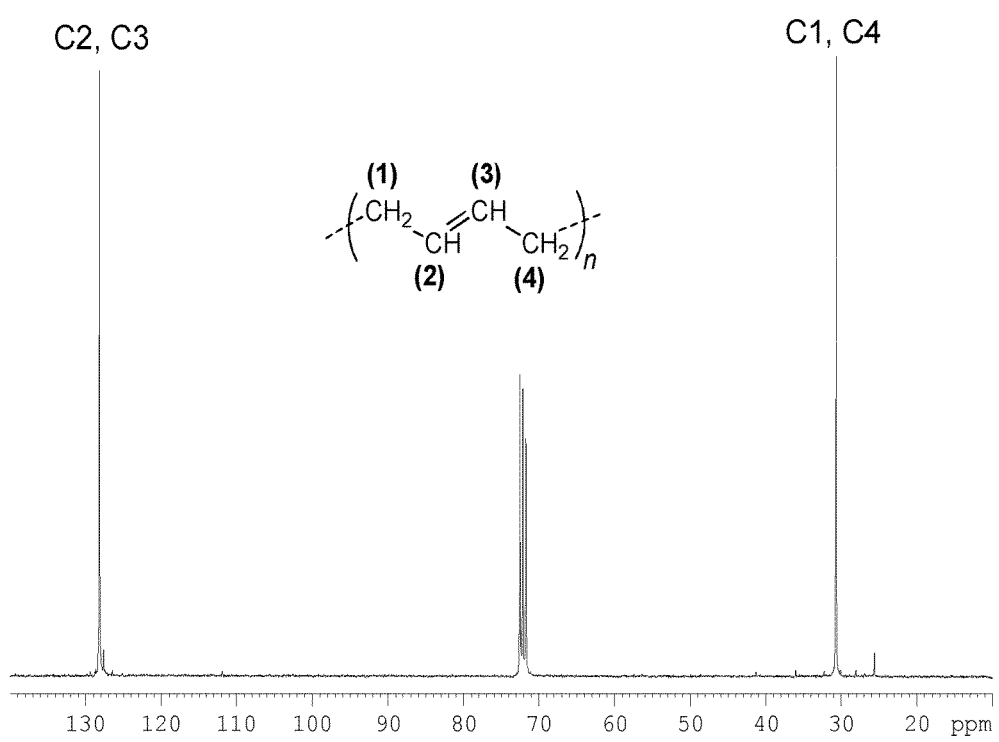
FIG. 9. Illustrated is a $^{13}$C-NMR spectrum of the polybutadiene obtained in Example 18.

FIG. 9 shows the $^{13}$C-NMR spectrum of the polybutadiene obtained.

Figure 13:
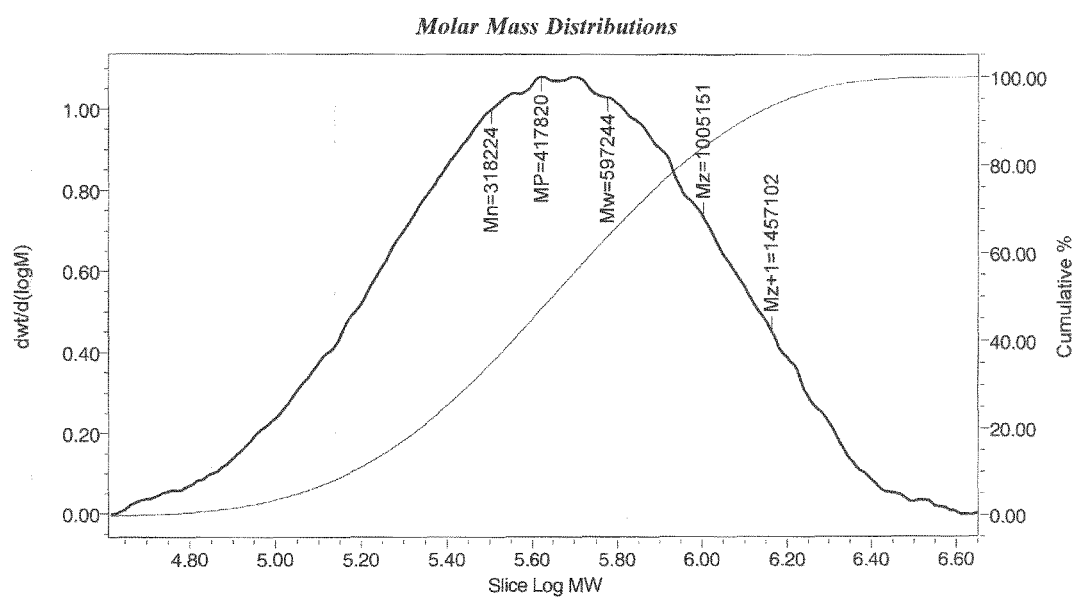
FIG. 13. Illustrated is a GPC diagram of the polybutadiene obtained in Example 18.

FIG. 13 shows the GPC diagram of the polybutadiene obtained.

Figure 18:
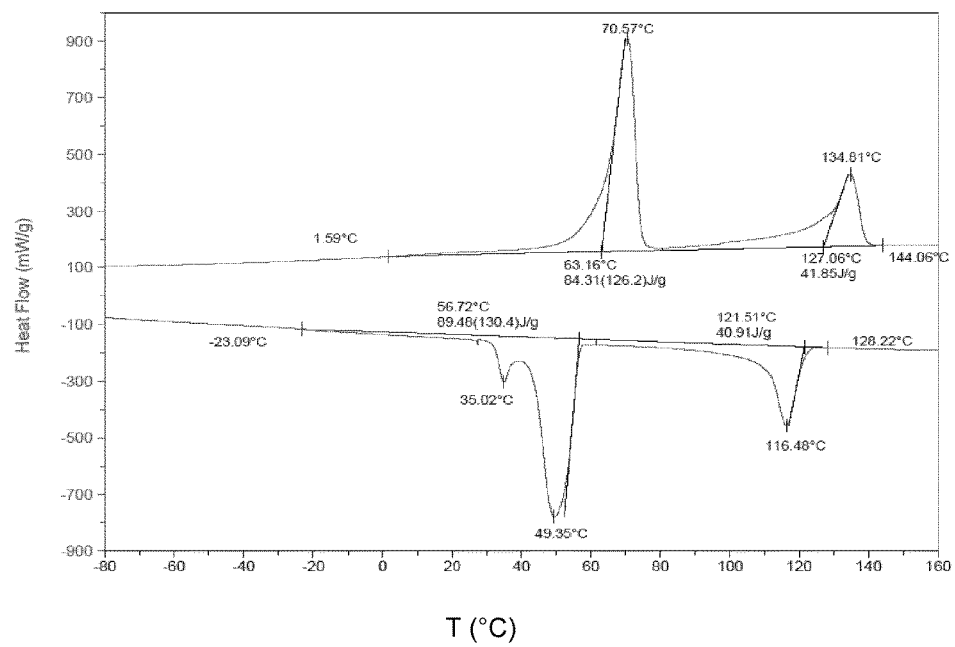
FIG. 18. Illustrated is a DSC diagram of the polybutadiene obtained in Example 18.

FIG. 18 shows the DSC diagrams of the polybutadiene obtained.

Example 19 (G1125)

Into a first 25 ml test tube were condensed, in the cold (−20° C.), 2 ml of 1,3-butadiene, equal to approximately 1.4 g. Subsequently, 9.3 ml of toluene were added and the temperature of the solution thus obtained was brought to 20° C. Subsequently, dry methylaluminoxane (MAOdry) in a toluene solution (10 ml; $3\times10^{-2}$ mol, equal to approximately 1.74 g) was added. Into a second 10 ml test tube were introduced the $ZrCl_3(L3)$ complex [sample MT-2] (2.7 ml of toluene solution at a concentration of 5 mg/ml; $3\times10^{-5}$ mol, equal to approximately 13.4 mg) obtained as described in Example 10 and di-iso-butyl-aluminium hydride (DIBAH) (3 ml of toluene solution at a concentration of 0.040 g/ml; $8.4\times10^{-4}$ mol, equal to approximately 120 mg): the whole was kept, under stirring, at room temperature, for 10 minutes, and the solution obtained was completely added to said first test tube. The whole was kept, under magnetic stirring, at 20° C., for 4 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 1.24 g of polybutadiene having a content of 1,4-trans units of 99%: further features of the process and of the polybutadiene obtained are shown in Table 1.

FIG. 6(*d*) shows the FT-IR spectrum of the polybutadiene obtained.

Example 20 (G1112)

Into a 25 ml test tube were condensed, in the cold (−20° C.), 2 ml of 1,3-butadiene, equal to approximately 1.4 g. Subsequently, 5.15 ml of toluene were added and the temperature of the solution thus obtained was brought to 20° C. Subsequently, methylaluminoxane (MAO) in a toluene solution (15.75 ml; $2.5\times10^{-2}$ mol, equal to approximately 1.45 g) was added, followed by the $ZrCl_3(L6)$ complex [sample MT-30] (4.1 ml of toluene solution at a concentration of 5 mg/ml; $3\times10^{-5}$ mol, equal to approximately 20.5 mg) obtained as described in Example 12. The whole was kept, under magnetic stirring, at 20° C., for 7 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 0.68 g of polybutadiene having a content of 1,4-trans units of 95%: further features of the process and of the polybutadiene obtained are shown in Table 1.

Figure 10:
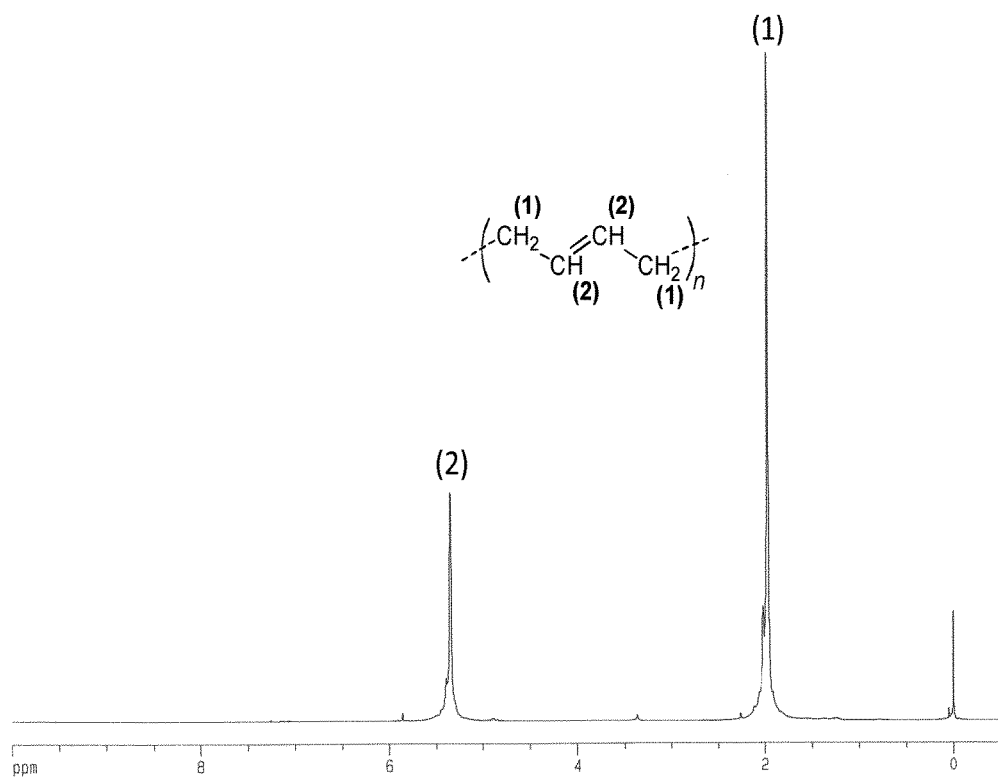
FIG. 10. Illustrated is a $^1$H-NMR spectrum of the polybutadiene obtained in Example 20.

FIG. 10 shows the $^1$H-NMR spectrum of the polybutadiene obtained.

Figure 11:
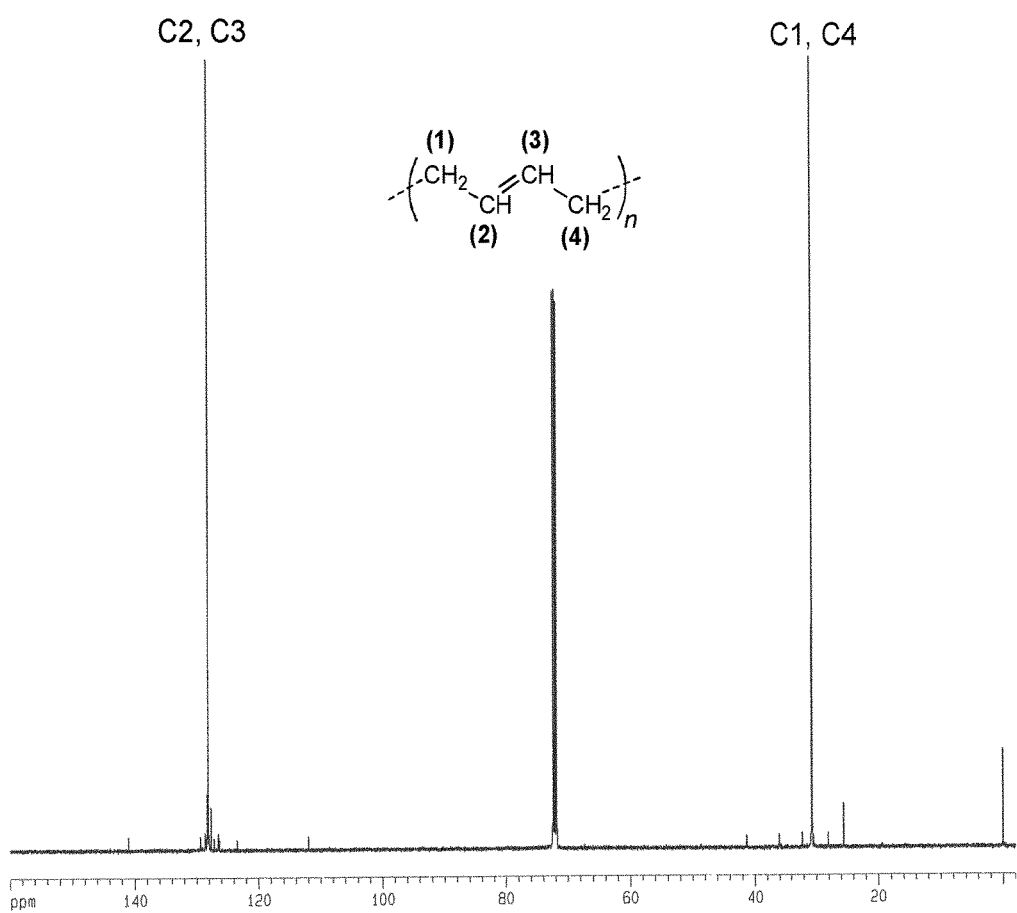
FIG. 11. Illustrated is a $^{13}$C-NMR spectrum of the polybutadiene obtained in Example 20.

FIG. 11 shows the $^{13}$C-NMR spectrum of the polybutadiene obtained.

Example 21 (MM21)

Into a first 25 ml test tube were condensed, in the cold (−20° C.), 2 ml of 1,3-butadiene, equal to approximately 1.4 g. Subsequently, 9.54 ml of toluene were added and the temperature of the solution thus obtained was brought to 20° C. Subsequently, dry methylaluminoxane (MAOdry) in a toluene solution (10 ml; $3\times10^{-2}$ mol, equal to approximately 1.74 g) was added. Into a second 10 ml test tube were introduced the $ZrCl_3(L6)$ complex [sample MT-30] (2.7 ml of toluene solution at a concentration of 5 mg/ml; $3\times10^{-5}$ mol, equal to approximately 13.44 mg) obtained as described in Example 12 and tri-iso-butyl-aluminium (TIBA) (3 ml of toluene solution at a concentration of 0.056 g/ml; $8.4\times10^{-4}$ mol, equal to approximately 167 mg): the whole was kept, under stirring, at room temperature, for 10 minutes, and the solution obtained was completely added to said first test tube. The whole was kept, under magnetic stirring, at 20° C., for 4 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 1.15 g of polybutadiene having a content of 1,4-trans units of 99%: further features of the process and of the polybutadiene obtained are shown in Table 1.

FIG. 6(*e*) shows the FT-IR spectrum of the polybutadiene obtained.

Figure 14:
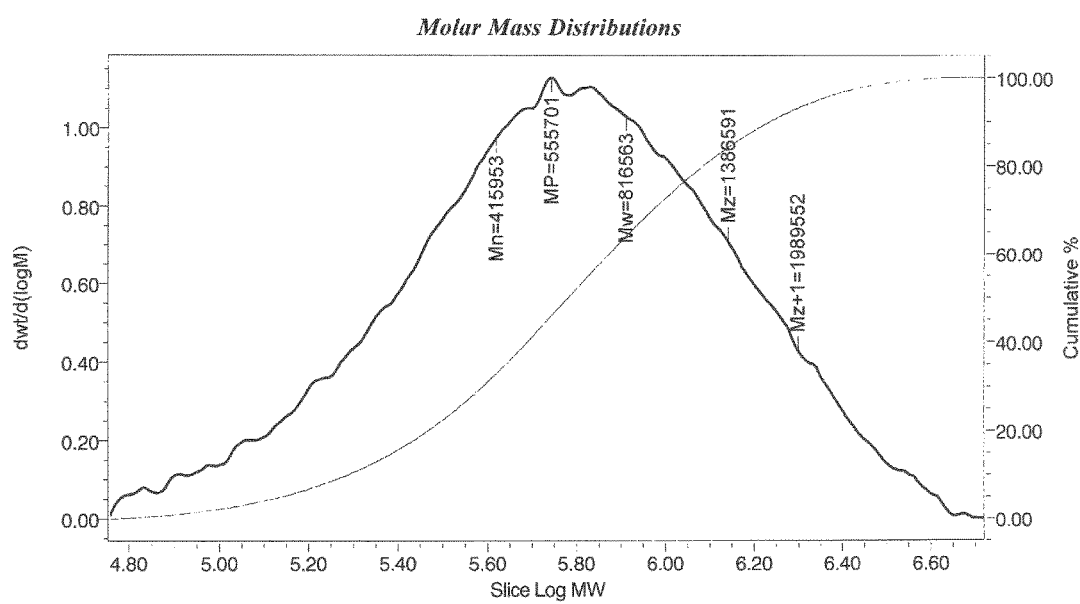
FIG. 14. Illustrated is a GPC diagram of the polybutadiene obtained in Example 21.

FIG. 14 shows the GPC diagram of the polybutadiene obtained.

Example 22 (G1120)

Into a 25 ml test tube were condensed, in the cold (−20° C.), 2 ml of 1,3-butadiene, equal to approximately 1.4 g.

Subsequently, 4.65 ml of toluene were added and the temperature of the solution thus obtained was brought to 20° C. Subsequently, methylaluminoxane (MAO) in a toluene solution (15.75 ml; $2.5 \times 10^{-2}$ mol, equal to approximately 1.45 g) was added, followed by the $ZrCl_3(L4)$ complex [sample MT-56] (4.6 ml of toluene solution at a concentration of 5 mg/ml; $5 \times 10^{-5}$ mol, equal to approximately 23 mg) obtained as described in Example 14. The whole was kept, under magnetic stirring, at 20° C., for 6 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 0.55 g of polybutadiene having a content of 1,4-trans units of 95%: further features of the process and of the polybutadiene obtained are shown in Table 1.

Figure 15:
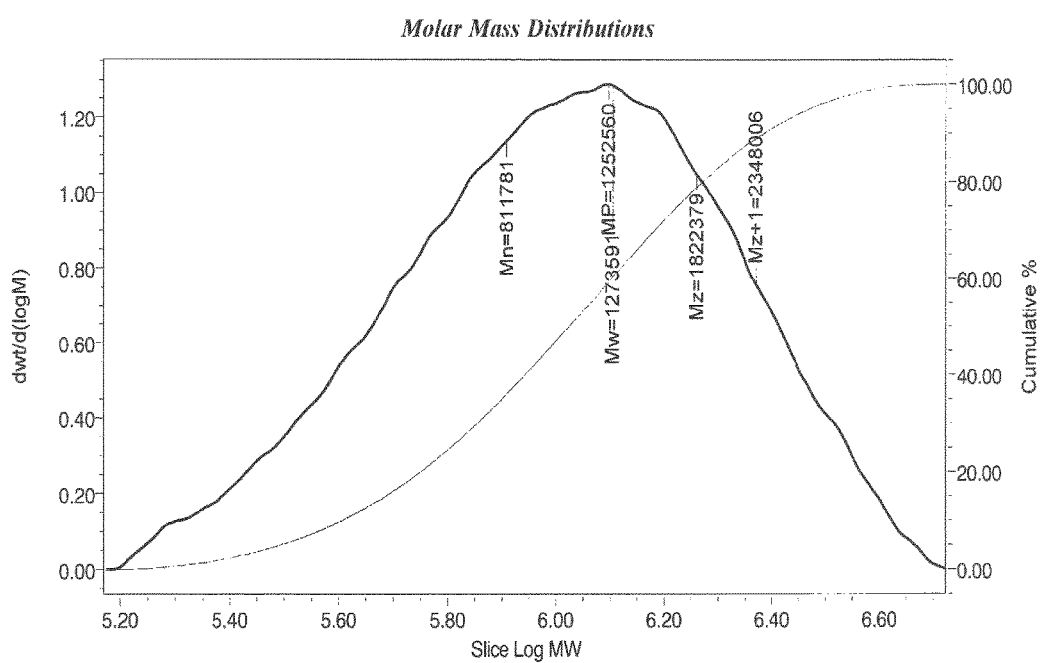
FIG. 15. Illustrated is a GPC diagram of the polybutadiene obtained in Example 22.

FIG. 15 shows the GPC diagram of the polybutadiene obtained.

Example 23 (G1121)

Into a 25 ml test tube were condensed, in the cold (−20° C.), 2 ml of 1,3-butadiene, equal to approximately 1.4 g. Subsequently, 2.15 ml of toluene were added and the temperature of the solution thus obtained was brought to 20° C. Subsequently, methylaluminoxane (MAO) in a toluene solution (15.75 ml; $2.5 \times 10^{-2}$ mol, equal to approximately 1.45 g) was added, followed by the $ZrCl_2(L5)_2$ complex [sample MT-81] (5.3 ml of toluene solution at a concentration of 5 mg/ml; $5 \times 10^{-5}$ mol, equal to approximately 26.4 mg) obtained as described in Example 15. The whole was kept, under magnetic stirring, at 20° C., for 5 hours. The polymerization was subsequently quenched by adding 2 ml of methanol containing a few drops of hydrochloric acid. The polymer obtained was subsequently coagulated by adding 40 ml of a methanol solution containing 4% of Irganox® 1076 antioxidant (Ciba), to obtain 1.36 g of polybutadiene having a content of 1,4-trans units of 94%: further features of the process and of the polybutadiene obtained are shown in Table 1.

Figure 16:
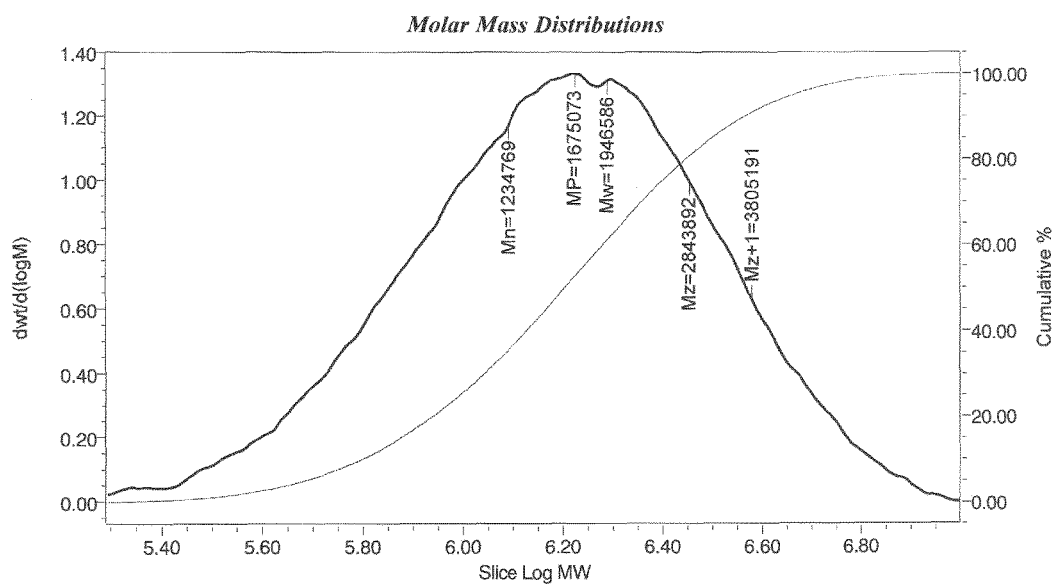
FIG. 16. Illustrated is a GPC diagram of the polybutadiene obtained in Example 23.

FIG. 16 shows the GPC diagram of the polybutadiene obtained.

Figure 17:
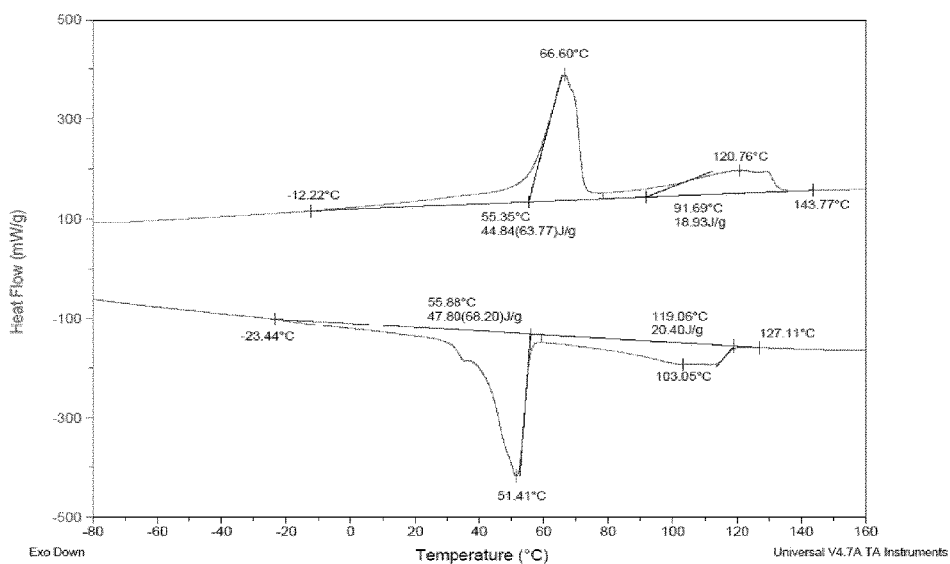
FIG. 17. Illustrated is a DSC diagram of the polybutadiene obtained in Example 23.

FIG. 17 shows the DSC diagrams of the polybutadiene obtained.

The invention claimed is:

1. Pyridine complex of zirconium having general formula (I):

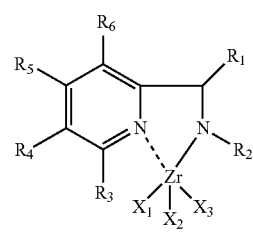

in which:
- $R_1$ and $R_2$, identical or different, represent a hydrogen atom; or are selected from linear or branched, optionally halogenated $C_1$-$C_{20}$, alkyl groups, optionally substituted cycloalkyl groups, or optionally substituted aryl groups;
- $R_3$, $R_4$, $R_5$ and $R_6$, identical or different, represent a hydrogen atom; or are selected from linear or branched, optionally halogenated $C_1$-$C_{20}$, alkyl groups, optionally substituted cycloalkyl groups, optionally substituted aryl groups, nitro groups, hydroxyl groups, or amino groups;
- $X_1$, $X_2$ and $X_3$, identical or different, represent a halogen atom; or are selected from linear or branched $C_1$-$C_{20}$, alkyl groups, —$OCOR_7$ groups or —$OR_7$ groups in which $R_7$ is selected from linear or branched $C_1$-$C_{20}$, alkyl groups; or one of $X_1$, $X_2$ and $X_3$ represents a group having general formula (II):

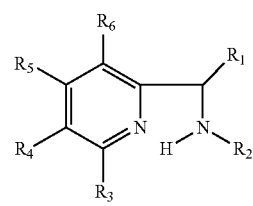

in which $R_1$, $R_2$, $R_3$, $R_4$, $R_5$ and $R_6$, have the same meanings described above.

2. Pyridine complex of zirconium having general formula (I) according to claim 1, in which:

TABLE 1

Polymerization of 1,3-butadiene using catalytic systems comprising complexes of zirconium

| Example | Time (min) | Yield (g) | Conversion (%) | 1,4-trans (%) | $M_w$ (g × mol$^{-1}$) | $M_w/M_n$ | $T_m^{(a)}$ (° C.) | $T_c^{(b)}$ (° C.) |
|---|---|---|---|---|---|---|---|---|
| 16 | 6 | 0.97 | 69.3 | 96 | 465500 | 2.8 | 119.9 | 103.8 |
| 17 | 7 | 0.63 | 45.0 | 95 | 347710 | 3.3 | 118.6 | 101.3 |
| 18 | 2 | 1.24 | 88.6 | 99 | 597200 | 1.9 | 134.8 | 116.5 |
| 19 | 4 | 0.84 | 60.0 | 99 | 752000 | 2.0 | 137.2 | 118.1 |
| 20 | 7 | 0.68 | 48.6 | 95 | 580500 | 2.6 | 133.9 | 116.1 |
| 21 | 4 | 1.15 | 82.1 | 99 | 816500 | 2.0 | 139.1 | 120.3 |
| 22 | 6 | 0.55 | 39.3 | 95 | 1273591 | 1.6 | 124.7 | 109.2 |
| 23 | 5 | 1.36 | 97.1 | 94 | 1950000 | 1.6 | 120.8 | 103.1 |

(a) melting point;
(b) crystallization temperature.

$R_1$ and $R_2$, identical or different, represent a hydrogen atom; or are selected from $C_1$-$C_{20}$ alkyl groups, optionally substituted aryl groups, or phenyl substituted with one or more methyl, iso-propyl, or tert-butyl groups;

$R_3$, $R_4$, $R_5$ and $R_6$, identical to each other, represent a hydrogen atom;

$X_1$, $X_2$ and $X_3$, identical or different, represent a halogen atom; or one of $X_1$, $X_2$ and $X_3$ represents a group having general formula (II):

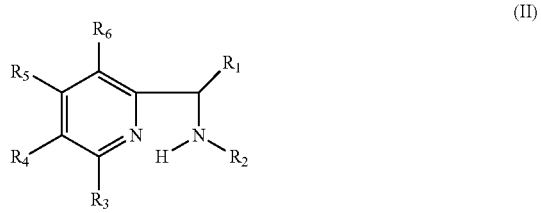
(II)

in which $R_1$, $R_2$, $R_3$, $R_4$, $R_5$ and $R_6$, have the same meanings described above.

3. Catalytic system for the (co)polymerization of conjugated dienes comprising:
  (a) at least one pyridine complex of zirconium having general formula (I) according to claim 1;
  (b) at least one co-catalyst selected from organic compounds of an element M' different from carbon, said element M' being selected from elements belonging to groups 2, 12, 13, or 14, of the Periodic Table of the Elements.

4. Catalytic system for the (co)polymerization of conjugated dienes according to claim 3, wherein said co-catalyst (b) is selected from ($b_1$) aluminium alkyls having general formula (IV):

$$Al(X')_n(R_8)_{3-n} \qquad (IV)$$

in which X' represents a halogen atom; $R_8$ is selected from linear or branched $C_1$-$C_{20}$ alkyl groups, cycloalkyl groups, or aryl groups, said groups being optionally substituted with one or more atoms of silicon or germanium; and n is an integer ranging from 0 to 2.

5. Catalytic system for the (co)polymerization of conjugated dienes according to claim 3, wherein said co-catalyst (b) is selected from ($b_2$) organo-oxygenated compounds of an element M' different from carbon belonging to groups 13 or 14 of the Periodic Table of the Elements.

6. Catalytic system for the (co)polymerization of conjugated dienes according to claim 3, wherein said co-catalyst (b) is selected from ($b_3$) compounds or mixtures of organo-metallic compounds of an element M' different from carbon able to react with the pyridine complex of zirconium having general formula (I), extracting from this a σ-linked substituent $X_1$, $X_2$ or $X_3$, to form on the one hand at least one neutral compound, and on the other an ionic compound consisting of a cation containing a metal (Zr) coordinated by a ligand, and of a non-coordinating organic anion containing the metal M', whose negative charge is delocalized on a multi-centric structure.

7. Catalytic system for the (co)polymerization of conjugated dienes according to claim 4, wherein said aluminium alkyls ($b_1$) having general formula (IV) are tri-ethyl-aluminium, tri-iso-butyl aluminium (TIBA), or di-iso-butyl aluminium hydride (DIBAH).

8. Catalytic system for the (co)polymerization of conjugated dienes according to claim 5, wherein said organo-oxygenated compounds ($b_2$) are selected from aluminoxanes having general formula (V):

$$(R_9)_2-Al-O-[-Al(R_{10})-O-]_p-Al-(R_{11})_2 \qquad (V)$$

in which $R_9$, $R_{10}$ and $R_{11}$, identical or different, represent a hydrogen atom, a halogen atom; or are selected from linear or branched $C_1$-$C_{20}$ alkyl groups, cycloalkyl groups, or aryl groups, said groups being optionally substituted with one or more atoms of silicon or germanium; and p is an integer ranging from 0 to 1000.

9. Catalytic system for the (co)polymerization of conjugated dienes according to claim 8, in which said organo-oxygenated compound ($b_2$) is methylaluminoxane (MAO) as such or in dry form (MAO-dry).

10. Catalytic system for the (co)polymerization of conjugated dienes according to claim 6, wherein said compounds and/or mixtures of compounds ($b_3$) are selected from organic compounds of aluminium or boron, represented by the following general formulae:

$[(R_C)_wH_{4-w}] \cdot [B(R_D)_4]^-$; $B(R_D)_3$; $Al(R_D)_3$; $B(R_D)_3P$;
$[Ph_3C]^+ \cdot [B(R_D)_4]^-$; $[(R_C)_3PH]^+ \cdot [B(R_D)_4]^-$;
$[Li]^+ \cdot [B(R_D)_4]^-$; $[Li]^+ \cdot [Al(R_D)_4]^-$ in which w is an integer ranging from 0 to 3, each $R_C$ group independently represents an alkyl group or an aryl group having from 1 to 10 carbon atoms and each $R_D$ group independently represents a partially or totally, fluorinated aryl group, having from 6 to 20 carbon atoms, P represents an optionally substituted pyrrole radical.

11. A process of (co)polymerizing conjugated dienes in the presence of the catalytic system of claim 4.

12. A process of polymerizing 1,3-butadiene in the presence of the catalytic system of claim 4.

* * * * *

UNITED STATES PATENT AND TRADEMARK OFFICE
CERTIFICATE OF CORRECTION

PATENT NO. : 10,059,724 B2
APPLICATION NO. : 15/512332
DATED : August 28, 2018
INVENTOR(S) : Guido Pampaloni et al.

Page 1 of 1

It is certified that error appears in the above-identified patent and that said Letters Patent is hereby corrected as shown below:

In the Claims

Column 40, Claim 10 – the formulae at Lines 36-38 should read as follows:

$[(R_C)_wH_{4-w}] \cdot [B(R_D)_4]^-$; $B(R_D)_3$; $Al(R_D)_3$; $B(R_D)_3P$; $[Ph_3C]^+ \cdot [B(R_D)_4]^-$;

$[(R_C)_3PH]^+ \cdot [B(R_D)_4]^-$;

$[Li]^+ \cdot [B(R_D)_4]^-$; $[Li]^+ \cdot [Al(R_D)_4]^-$

Signed and Sealed this
Sixth Day of November, 2018

Andrei Iancu
*Director of the United States Patent and Trademark Office*